United States Patent
Anderson

(10) Patent No.: US 12,422,295 B2
(45) Date of Patent: Sep. 23, 2025

(54) SYSTEM AND METHOD FOR DETERMINING CONTENT UTILIZING EXTERNALLY MOUNTED CONTAINER MONITORING SYSTEM

(71) Applicant: BARREL PROOF TECHNOLOGIES LLC, Murfreesboro, TN (US)

(72) Inventor: Brian Richard Anderson, Murfreesboro, TN (US)

(73) Assignee: BARREL PROOF TECHNOLOGIES LLC, Murfreesboro, TN (US)

( * ) Notice: Subject to any disclaimer, the term of this patent is extended or adjusted under 35 U.S.C. 154(b) by 0 days.

(21) Appl. No.: 19/080,723

(22) Filed: Mar. 14, 2025

(65) Prior Publication Data
US 2025/0244158 A1    Jul. 31, 2025

Related U.S. Application Data

(63) Continuation-in-part of application No. 19/013,859, filed on Jan. 8, 2025, which is a continuation-in-part of application No. 18/818,539, filed on Aug. 28, 2024, now Pat. No. 12,228,525, and a continuation-in-part of application No. 18/800,279, filed on Aug. 12, 2024, now Pat. No. 12,228,445, said application No. 18/818,539 is a continuation-in-part of application No. 18/424,758, filed on Jan. 27, 2024, now Pat. No. 12,117,329, said application No. 18/800,279 is a continuation-in-part of application No. 18/424,758, filed on Jan. 27, 2024, now Pat. No. 12,117,329.

(51) Int. Cl.
*G01F 23/284*    (2006.01)

(52) U.S. Cl.
CPC .................... *G01F 23/284* (2013.01)

(58) Field of Classification Search
CPC ................ G01F 23/284; C12G 1/00
See application file for complete search history.

(56) References Cited

U.S. PATENT DOCUMENTS 1,854,122 A * 4/1932 Eaton .................. G01S 7/4026
                                                342/126
3,953,856 A * 4/1976 Hammack ............. G01S 3/46
                                                342/126

(Continued)

OTHER PUBLICATIONS

U.S. Appl. No. 18/424,758, filed Jan. 27, 2024.

(Continued)

*Primary Examiner* — Peter M Bythrow

(57) ABSTRACT

A system for determining a fill level of at least one of a content within a container wherein the fill level of the at least one content is determined based on the reception of a time of return of a transmitted signals wherein the transmitted signals are frequency varying within a transmission window. The frequency variation may be continuous or patterned. The device herein disclosed is applicable to a wide spectrum of configurations to determine a content, whether liquid, mash or solid within the container wherein the container may be associated with a barrel or container associated with alcohol production, or containers involved in the retention of other types of materials or content, such as but not limited to, septic tanks, waste management systems, water towers, etc.

21 Claims, 24 Drawing Sheets

(56) References Cited

U.S. PATENT DOCUMENTS

| | | | | |
|---|---|---|---|---|
| 6,002,357 | A * | 12/1999 | Redfern | G01S 13/88 342/126 |
| 6,298,008 | B1 * | 10/2001 | Lyon | G01S 7/40 367/908 |
| 6,995,706 | B2 * | 2/2006 | Ohlsson | G01S 13/24 342/134 |
| 7,173,436 | B2 * | 2/2007 | Edvardsson | G01F 23/284 342/124 |
| 7,304,601 | B1 * | 12/2007 | Edvardsson | G01S 13/10 342/123 |
| 7,525,476 | B1 * | 4/2009 | Delin | G01S 7/4056 73/304 R |
| 7,821,444 | B2 * | 10/2010 | Hall | G01S 13/88 342/124 |
| 8,884,632 | B2 * | 11/2014 | Klofer | G01F 23/284 324/637 |
| 9,217,660 | B2 * | 12/2015 | Zlotnick | G01S 13/003 |
| 9,377,340 | B2 * | 6/2016 | Hägg | H04Q 9/00 |
| 9,518,859 | B2 * | 12/2016 | Bartov | G01F 23/2962 |
| 10,260,929 | B2 * | 4/2019 | Kassubek | G01S 13/878 |
| 10,775,221 | B2 * | 9/2020 | Blomberg | G01S 7/354 |
| 10,788,351 | B2 * | 9/2020 | Welle | G01S 7/032 |
| 10,801,873 | B2 * | 10/2020 | Westerling | G01F 23/284 |
| 2005/0179584 | A1 * | 8/2005 | Ohlsson | G01S 7/023 342/159 |
| 2006/0201246 | A1 * | 9/2006 | Rolfes | G01B 15/04 73/290 V |
| 2007/0028684 | A1 * | 2/2007 | Benz | G01F 23/284 73/314 |
| 2008/0101158 | A1 * | 5/2008 | Hosseini | G01F 23/2962 367/87 |
| 2008/0272968 | A1 * | 11/2008 | Muller | G01F 23/284 343/703 |
| 2009/0007627 | A1 * | 1/2009 | Perl | G01F 23/2962 73/1.73 |
| 2010/0090883 | A1 * | 4/2010 | Chen | G01F 23/284 342/124 |
| 2010/0101317 | A1 * | 4/2010 | Ashrafzadeh | G01F 23/26 702/188 |
| 2011/0193567 | A1 * | 8/2011 | Klofer | G01F 23/284 324/642 |
| 2011/0272866 | A1 * | 11/2011 | Shameli | B22D 2/003 266/78 |
| 2012/0281096 | A1 * | 11/2012 | Gellaboina | G01S 15/88 342/179 |
| 2014/0208845 | A1 * | 7/2014 | Zlotnick | G01S 3/808 73/290 V |
| 2015/0007655 | A1 * | 1/2015 | Skowaisa | G01F 1/663 73/198 |
| 2015/0009063 | A1 * | 1/2015 | Korsbo | G01F 23/284 342/124 |
| 2015/0198474 | A1 | 7/2015 | Howard | |
| 2017/0141453 | A1 * | 5/2017 | Waelde | G01S 13/88 |
| 2017/0350744 | A1 * | 12/2017 | Gerson | G01F 23/18 |
| 2019/0316951 | A1 * | 10/2019 | McCormick | G01F 23/2845 |
| 2022/0252444 | A1 * | 8/2022 | Kincaid | G01F 23/68 |

OTHER PUBLICATIONS

U.S. Appl. No. 18/800,279, filed Aug. 12, 2024.
U.S. Appl. No. 18/818,539, filed Aug. 28, 2024.
U.S. Appl. No. 19/013,859, filed Jan. 8, 2025.

* cited by examiner

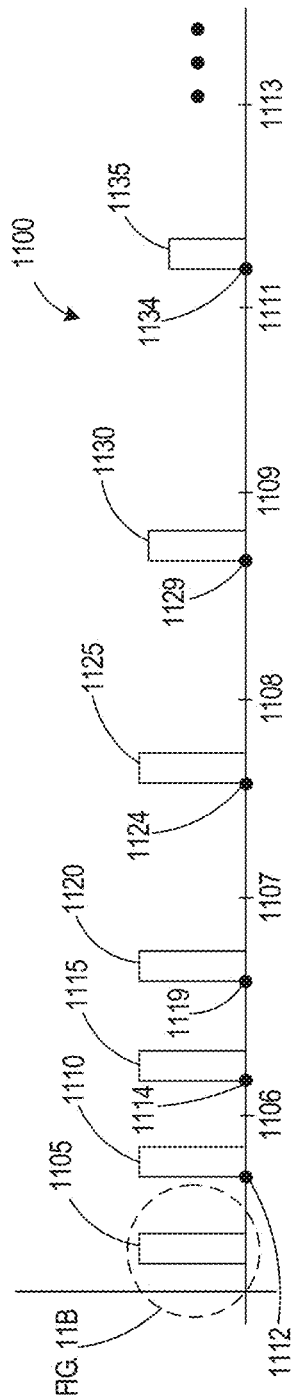
FIG. 11A
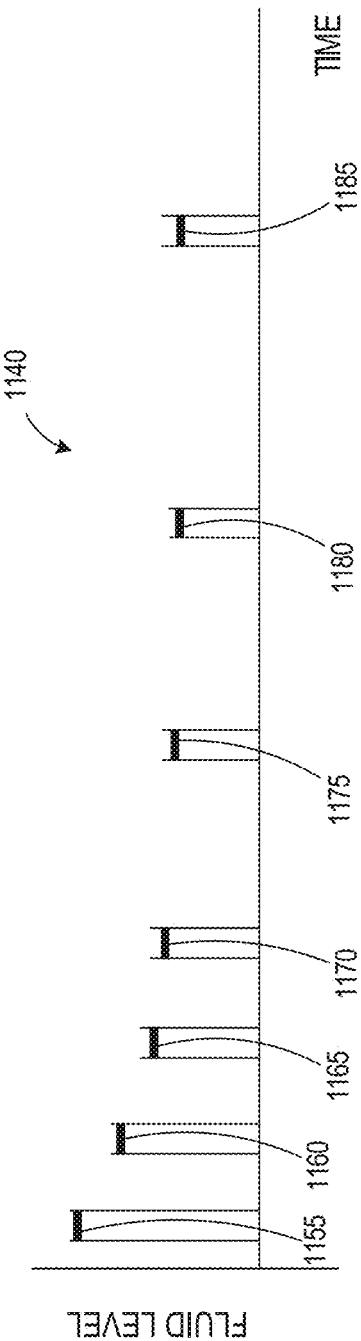
FIG. 11C
FIG. 11B
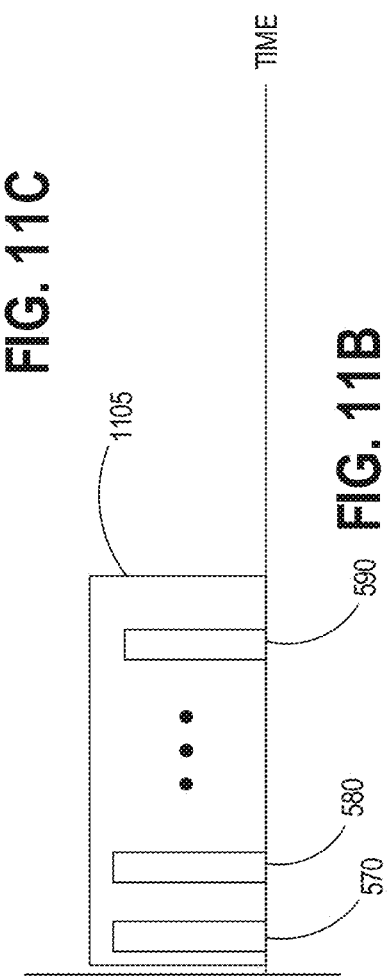

SYSTEM AND METHOD FOR DETERMINING CONTENT UTILIZING EXTERNALLY MOUNTED CONTAINER MONITORING SYSTEM

CROSS-REFERENCE TO RELATED APPLICATIONS

This application is a Continuation-in-part of, and claims the benefit of U.S. application Ser. No. 19/013,859, titled "SYSTEM AND METHOD FOR DETERMINING FLUID LEVEL AND/OR ALCOHOL CONTENT UTILIZING EXTERNALLY MOUNTED CONTAINER MONITORING SYSTEM" filed on Jan. 8, 2025, which is a Continuation-in part and claims of the benefit of U.S. application Ser. No. 18/800,279, titled "SYSTEM AND METHOD FOR DETERMINING ALCOHOL CONTENT WITHIN CONTAINER UTILIZING CONTAINER MONITORING SYSTEM," filed on Aug. 12, 2024, and U.S. application Ser. No. 18/818,539, titled "SYSTEM AND METHOD FOR DETERMINING ALCOHOL CONTENT UTILIZING CONTAINER MONITORING SYSTEM," filed on Aug. 28, 2024, both of which having claimed, as Continuation-in-part applications, the benefit and earlier filing date of U.S. application Ser. No. 18/424,758, titled "CONTAINER MONITORING SYSTEM AND METHOD THEREOF," filed on Jan. 27, 2024. This application incorporates by reference, herein, the entire contents of the above referred-to patent applications.

TECHNICAL FIELD

This disclosure relates generally to the field of fluid management and measurement of liquid content within containers and alcohol determination based on the fluid content.

BACKGROUND

Containers, such as barrels, have been used for centuries for the containment and processing of fermenting liquids. Whether the enclosed liquid is wine, beer or spirits, the wooden containers (or barrels) represent an industrial standard for the aging and fermentation of the contained liquid. In many cases, the fermenting liquid may be retained within the same wooden barrel for many years, wherein the increase in length of time (i.e., in storage) impairs different favor, quality and cost to the contained liquid. For example, spirits are measured by the duration of their aging process, wherein the longer the contained product is aged, the more expensive the value of the product becomes. For example, a 200-year-old Napoleon brandy is significantly more expensive than a 2-year-old brandy by the same manufacturer, as the brandy has been fermenting in the barrel for a significantly longer period of time.

However, issues regarding the use of wooden barrels are well-known in the art. For example, fermenting liquid within a barrel is prone to two types of losses. The first being evaporation of the liquid within the barrel and the second being absorption by the wooden elements comprising the barrels.

In many cases, the barrels, once filled, are retained within a known position, whether vertical or horizontal, for the duration of their intended aging process. During this time, inspection of the contained liquid (quality, level and alcohol content (or measurement)) may occur by the insertion of one or more types of measurement tools into the barrel.

However, insertion of the measurement tool may introduce air or other contaminants that may alter the quality of the contained liquid. In addition, the repeated insertion of the measurement tools increases the amount of labor required to monitor the critical aspects of the fermentation process (i.e., alcohol production).

Furthermore, the measurement of fluid loss within a barrel or container is an important factor in the whiskey industry as distillers are required to report to Tax and Trade Bureaus container fill volume.

In addition, alcohol content (or Proof) is extremely important to know as distillers are required to follow stringent rules for the classification of different spirits.

For example, to be classified as a Bourbon whiskey the liquid at bottling must have a minimum alcohol content of 40 percent by volume (ABV), Generally, typically bottled Bourbon is between 40 and 60 percent ABV, whereas the liquid entered into the barrel for aging should have an ABV of no greater 62.5 percent ABV. For a general Whiskey, the liquid at bottling must have a minimum alcohol content of 40 percent ABV.

As mentioned above, the conventional methods for determining fluid level and alcohol content is labor intensive as it requires the sampling of the aging fluid by drawing a sample from the container (i.e., opening the barrel, which may introduce air into the container), measuring the sample's temperature, using a hydrometer or alcoholmeter to measure alcohol content, and adjusting the reading based on temperature. Alternatively, more modern analytical methods, such as gas chromatography or near-infrared spectroscopy, may be utilized to determine alcohol content. However, while these methods may provide highly accurate reading, they are more expensive and require specialized equipment.

In still another aspect, wherein container fill level is required to prevent exceeding capacity and also prevent overflow and damage, the conventional methods of such determination is both time-consuming and invasive.

Hence, there is a need in the industry for a non-intrusive method and system for obtaining measurements of the level of the contents of a container in order to determine at least one of a level of fluid and a content, wherein invasive probes or manual inspection or, even guesswork is removed.

SUMMARY

Herein disclosed is a system for determining a fill level of at least one of a content within a container wherein the fill level of the at least one content is determined based on the reception of a time of return of a transmitted signals wherein the transmitted signals are frequency varying with the transmission window. The frequency variation may be continuous or patterned. The frequency variation may be continuous or patterned. The device herein disclosed is applicable to a wide spectrum of configurations to determine a content, whether liquid, mash or solid within the container wherein the container may be associated with a barrel or container associated with alcohol production, or containers involved in the retention of other types of materials or content, such as but not limited to, septic tanks, waste management systems, water towers, etc.

BRIEF DESCRIPTION OF THE DRAWINGS

The advantages, nature, and various additional features of the invention will appear more fully upon consideration of the illustrative embodiments described in detail in connection with the accompanying drawings, where like or similar reference numerals are used to identify like or similar elements throughout the drawings.

FIGS. 11A-11C illustrate exemplary signal transmission and signal return graphs as a function of time in accordance with one aspect of the invention.

Figure 1:
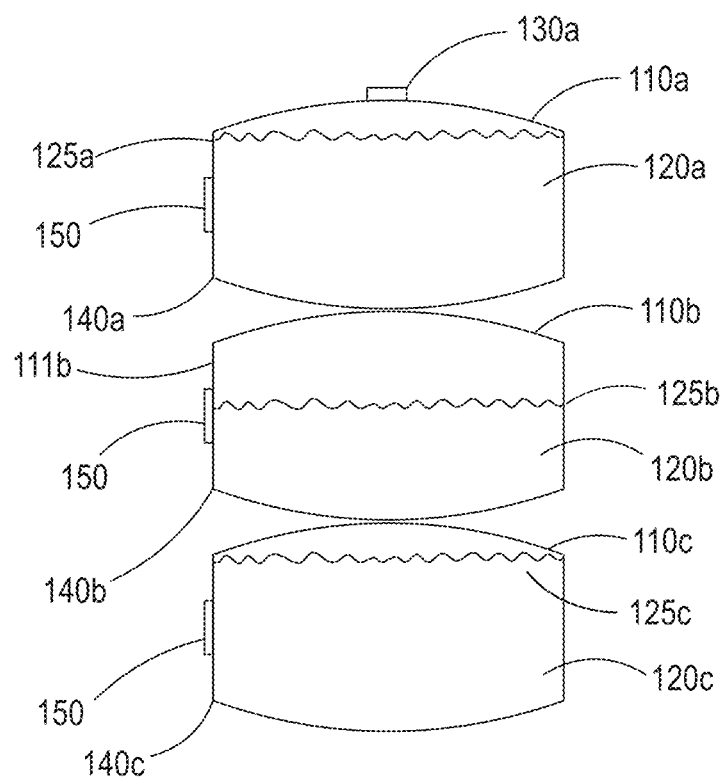
FIG. 1 illustrates a first conventional configuration for storing a plurality of barrels and the liquid contained therein.

It is to be understood that the figures, which are not drawn to scale, and descriptions of the present invention described herein have been simplified to illustrate the elements that are relevant for a clear understanding of the present invention, while eliminating, for purposes of clarity, many other elements. However, because these omitted elements are well-known in the art, and because they do not facilitate a better understanding of the present invention, a discussion of such elements are not provided herein. The disclosure, herein, is directed also to variations and modifications known to those skilled in the art.

DETAILED DESCRIPTION

Note that the specific embodiments given in the drawings and following description do not limit the disclosure. On the contrary, they provide the foundation for one of ordinary skill to discern the alternative forms, equivalents, and modifications that are contemplated by the inventors and encompassed in the claim scope.

Numerous alternative forms, equivalents, and modifications will become apparent to those skilled in the art once the above disclosure is fully appreciated. It is intended that the claims be interpreted to embrace all such alternative forms, equivalents, and modifications where applicable.

Disclosed herein are an apparatus and associated method implementations related to determining a liquid level within a barrel based on a system, located external to the barrel, configured to transmit a signal into the barrel and processing signals, reflected by the contained liquid, wherein the characteristics of the reflected signal (e.g. distance and time traveled) may be used to determine the presence of the liquid; determining a level of fluid within the barrel as a function of at least one of the distance and time traveled by the transmitted/reflected signal, determining a fluid level within the barrel and determining, as a function of at least the determined level of the fluid within the barrel and the physical dimensions of the barrel, the volume of fluid within the barrel.

Disclosed herein are an apparatus and associated method implementations located external to the barrel for determining an alcohol content within a barrel based on a system configured to transmit a signal (i.e., a measurement signal) into the barrel and processing signals, reflected by the contained liquid, wherein the characteristics of the reflected signal (e.g. signal strength, frequency, phase, distance and/or time traveled) may be used to determine the presence of the liquid and the alcohol content of the liquid, wherein determination of a level of fluid within the barrel may be used to determine which of a plurality of signals are transmitted into the barrel.

In one aspect of the invention, the system disclosed may comprise a modular device consisting of a motherboard, a specialized breakout board (chips), a data transmission module, a power source and at least one transmit and/or receiving antenna. The system may be attached to the face of an enclosed container (e.g., a whiskey barrel, wine barrel, beer barrel) with an antenna array that is suitable for transmitting signals in at least one of a Millimeter Wave (MM Wave)

range, or a radio frequency range (i.e., Institute of Electronic and Electrical Engineers (IEEE) designated bands HF through W, and other wavelength ranges). In one aspect of the invention, the system and method disclosed any utilize a millimeter wave transmission system in a wavelength band of 57-64 GHz. In another aspect of the invention, a transmission system may operate in one or more of an ISM (Industrial, scientific, and medical) wavelength band that would avoid interference with other types of electronic equipment.

In one aspect of the invention, each of the at least one antenna may be configured to emit or transmit a signal at a same known wavelength within one or more of the referred to wavelength bands. In one aspect of the invention, each of the at least one antenna may be configured to transmit a signal at a different known frequency (or wavelength) within one or more of the referred to wavelength bands. In one aspect of the invention, each of the at least one antenna may be configured to transmit at least one signal at one or more frequencies within one or more different known frequency or wavelength bands.

In one aspect of the invention, one or more characteristics (e.g., signal strength, frequency, phase, distance and/or time traveled) of the signals reflected by the contained fluid or liquid, may be used to determine a level of the contained fluid based at least on a position of one or more of the antennas receiving the reflected signals and subsequently the alcohol content of the liquid within the barrel.

In one aspect of the invention, the signal strength of the signals reflected by the contained fluid or liquid, may be used to determine the level of the contained fluid based at least on a position of one or more of the antennas receiving the reflected signals.

In one aspect of the invention, measurements regarding the signal strength and determined fluid level (and volume) may be relayed to a communications hub via one or more transmissions protocols and exported wirelessly (cellular, Wi-Fi) or over a wired Internet connection to a common database wherein reports may be derived. In another aspect of the invention, measurements regarding signal strength and determined fluid level (and/or volume) may be relayed by a near-field communication transmission (e.g., RFID, BLUETOOTH, etc.) that enable periodic monitoring of the determined fluid level and/or volume.

In one aspect of the invention, consultative data analysis reports may be created to assist a manufacturer/consumer with making actionable business decisions based upon results.

In accordance with the principles of the invention, the system and method disclosed may utilize a Millimeter wave transmission system (30 GHz-300 GHz) and an appropriately scaled (frequency selective) antennas to determine a level of the liquid inside of an enclosed container (e.g., a whiskey barrel).

In one aspect of the invention, by measuring the liquid level over time, a manufacturer/consumer may determine fluid internal volume at any given period. In accordance with the principles of the invention, while barrel technology is referred to, it would be understood by those skilled in the art that the system and method disclosed may be utilized to determine the fluid level in any enclosed system used containing liquid.

In one aspect of the invention, a method is disclosed for determination of an alcohol content of a liquid within an enclosed barrel wherein the alcohol content is based on an initial alcohol content and one or more environmental factors, such as location, temperature, environment conditions, etc.

In one aspect of the invention, a method is disclosed for the determination of an alcohol content of a contained fluid based on a determination of evaporation and/or absorption of the fluid and an extrapolation from a known initial level.

In one aspect of the invention, a method is disclosed wherein a determination of a loss of fluid within an enclosed container is utilized to determine an alcohol content of the fluid considering one or more environmental factors.

In accordance with the principles of the invention, while barrel technology is referred to, it would be understood by those skilled in the art that the system and method disclosed may be utilized to determine the fluid level in any enclosed system containing liquid.

In one aspect of the invention, a method is disclosed for the determination of an alcohol content of a contained fluid based on an evaluation of at least one variation in at least one characteristic (e.g., signal strength change, frequency shift, phase shift, change in distance and/or time traveled, etc.) of at least one reflection of a signal transmitted in at least one frequency or wavelength band.

Each of the foregoing implementations can be employed individually or in conjunction.

FIG. 1 illustrates a first conventional configuration for storing a plurality of barrels and the liquid contained therein.

Conventionally barrels 110a, 110b, 110c, may be filled with a liquid 120a, 120b, 120c, respectively, and stacked horizontally in racks (not shown). The implementation depicted by FIG. 1 shows the exemplary respective liquid levels 125a, 125b, 125c of liquids 120a, 120b, 120c. Access to barrels 110a, 110b, 110c, is conventional though a bung 130 individually configured in each barrel 110 (of which only bung 130a associated with barrel 110a is shown). In the depicted example the bung 130a is positioned on a side surface of the corresponding barrel 110a. Although only bung 130a associated with barrel 110a is shown, it would be recognized that bung 130 (130a, 130b, 130c) is associated with each of the illustrated barrels 110a, 110b, 110c.

Generally, the bung 130 (e.g., 130a, 130b, 130c) enables a tester (not shown) to access the liquid 120a, 120b, 120c in a corresponding one of barrels 110a, 110b, 110c. As previously discussed, the conventional manner of testing is to insert an object (e.g., a pipette,) into the bung hole 130, wherein liquid is collected in the pipette and removed from barrel 110. The liquid may then be tested to determine quality and the level of the liquid within the barrel using a graduated scale on the pipette.

However, as discussed above, the opening of the bung 130 to insert the pipette into the container 110 to test the contained liquid 120 introduces air and, possibly, other contaminants into the contained liquid. The introduced air may alter the quality of the contained liquid.

Accordingly, container monitoring system 150, disclosed herein, resolves the issues that are known to occur with the conventional means for testing the liquid level within the container. Container monitoring system 150 provides a non-invasive method for determining a level of a contained liquid 120a within barrel 110a, through its inclusion or introduction onto a face surface 140 of each of the illustrated containers or barrels 110a.

Although face surface 140a associated with barrel 110a is shown, it would be recognized that monitoring system 150 may be applied to the face surface 140 of barrels 110b, 110c to provide a non-invasive method for determining a level of a contained liquid (120b, 120c) within barrels 110b, 110c, respectively.

Figure 2:
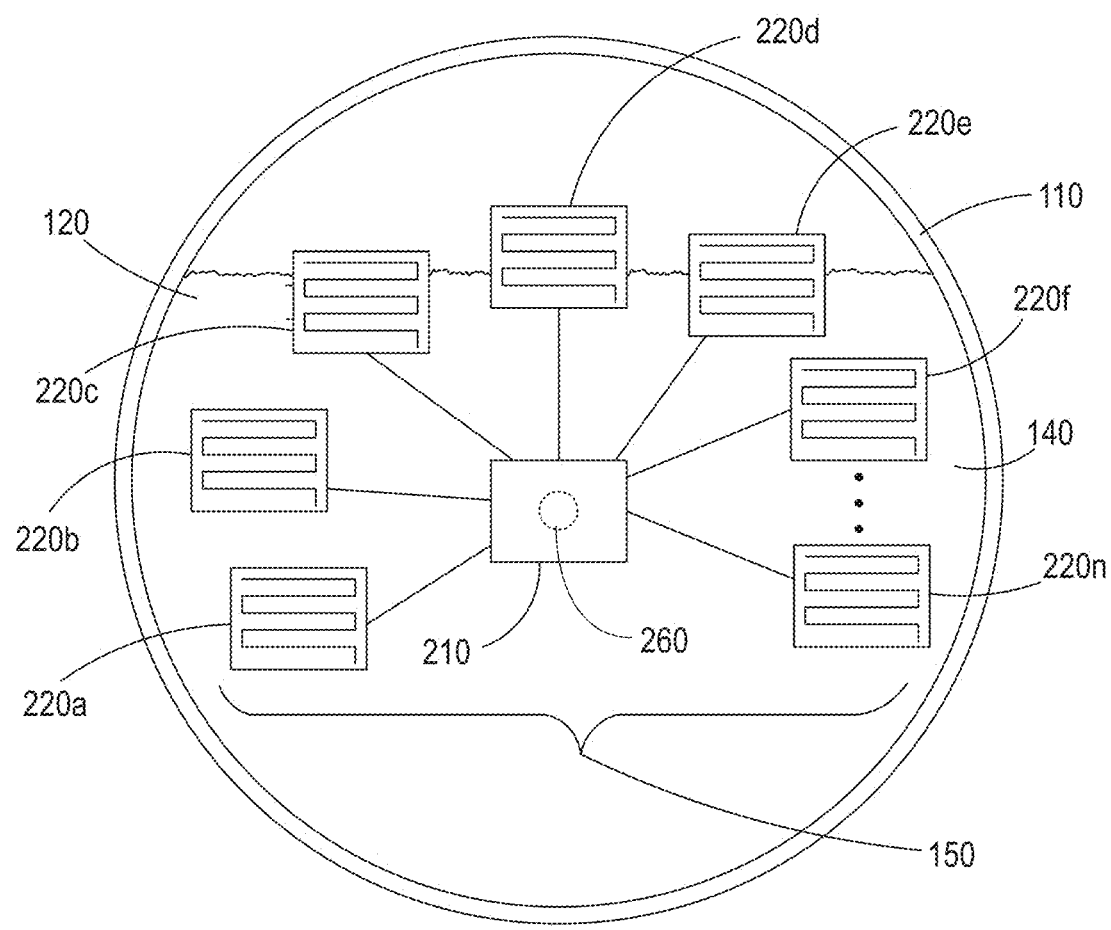
FIG. 2 illustrates a first exemplary embodiment of a system for determining liquid content within a barrel in accordance with the principles of the invention.

FIG. 2 illustrates a first exemplary embodiment of a monitoring system 150 in accordance with the principles of the invention.

In accordance with the principles of the invention, monitoring system 150 comprising processing section 210 and a plurality of antennas 220 (220a, 220b, 220c . . . 220n) which are positioned on a face surface 140 of a corresponding container or barrel 110.

In accordance with the illustrated aspect of the invention, monitoring system 150 is arranged circumferentially (a "wagon wheel" configuration) about the face surface 140 of barrel 110, wherein processing system 210 is at a center (or hub) of the plurality of illustrated antennas 220a, 220b, . . . 220n.

In accordance with this aspect of the invention, the position of each of the illustrated antennas 220a, 220b . . . 220n with respect to a center position 260 of face surface 140 is known and in a symmetrical relationship. For example, in this illustrated aspect, antennas 220a, 220b . . . 220n may be positioned on face 140 in a conventional "clock" formation. That is, antenna 220d is illustrated as being positioned in a 12 o'clock position with respect to center 260, antenna 220e is illustrated as being positioned at a 1 o'clock position with respect to center 260. Antenna 220f is illustrated as being positioned at a 2 o'clock position with respect to center 260 and antenna 220n may be positioned at a 4 o'clock position with respect to center 260. Similarly, antennas 220c, 220b and 220a may be positioned at 11 o'clock, 10 o'clock and 8 o'clock positions, respectively, with respect to center 260. In accordance with the principles of the invention, the positioning of the illustrated antennas establishes a relationship between a reference point (i.e., center point 260) and each of the antennas that may be used to determine a level of fluid 120 within container 110.

In another aspect of the invention, the plurality of illustrated antennas may be arranged in a physically, (i.e., non-systematical) relation, wherein antennas 220d, 220e, 220f, and 220n may be positioned as discussed above (12, 1, 2, 4 o'clock, respectively) and antennas 220c, 220b and 220a may be positioned at 11:30 o'clock, 10:30 o'clock and 8:30 o'clock positions, respectively with respect to center 260. In accordance with the principles of the invention, the positioning of the antennas 220a . . . 220n in this manner provides for a refined determination of the level of fluid 120 within container 110, as will be discussed.

In one aspect of the invention, processing system 210 provides signals to a corresponding one of the antenna 220a, . . . 220n, which operates as a transmitting antenna to transmit the signals through face 140 toward liquid 120 contained within barrel 110. The corresponding antenna 220a . . . 220n, may then operate as a receiving antenna to receive a reflection of the transmitted signal, which is caused by the interaction of the transmitted signal with the contained liquid 120.

In one aspect of the invention, antennas 220a, 220b, . . . 220n may be omni-direction antennas that emit (or transmit) signals over a wide field of view (e.g., toward and away from face 140). In another aspect of the invention, antennas 220a, 220b . . . 220n may be directional antennas that emit (or transmit) signals in a very limited field of view (e.g., toward face 140). In still another aspect of the invention antennas 220a, 220b . . . 220n may be highly directional antennas with narrow beams widths that emit (or transmit) signals in a limited and narrow field of view (e.g., toward face 140 with 1-degree beamwidth).

In one aspect of the invention, antennas 220a, 220b . . . 220n may each be configured as transmitting and receiving antenna, wherein original signals provided by processing system 210 are transmitted by antennas 220a . . . 220n and reflection signals, captured by antennas 220a . . . 220n), are provided to processing system 210. In another aspect of the invention, selected ones of the illustrated antennas 220a, 220b . . . 220n may operate as transmitting antennas to transmit signals into container 110 and selected other ones of the illustrated antennas 220a, 220b . . . 220n may operate as receiving antenna to capture reflections of the transmitted signals. The antennas designated as transmitting antennas receive signals from processing system 210 and receiving antenna provide signals to processing system 210.

In addition, antennas designated as transmitting antennas may comprise omni-directional or highly directional antenna and antennas designated as receiving antennas may be narrow beam width directional antennas.

In one aspect of the invention, a single antenna may be designated as a transmitting antenna (e.g., 220d) and the remaining of the illustrated antennas (220a, 220b, 220c, 220e . . . 220n) may be designated as receiving antenna. In this case, a single "ping" from the one transmitting antenna may be detected by a plurality of receiving antennas and the results of the detected reflections may be utilized to determine a level of fluid contained. In still another aspect of the invention, the single transmitting antenna may periodically transmit a "ping" and each of the designated receiving antenna may be selectively "turned-on" to enable the 'turned-on] receiving antenna to receive a reflection of the transmitted signal.

Although, monitoring system 150 is shown with processing system 210 as a central hub, it would be recognized by those skilled in the art that processing system 210 may be placed at any position on face 140 without altering the scope of the invention claimed.

Figure 3:
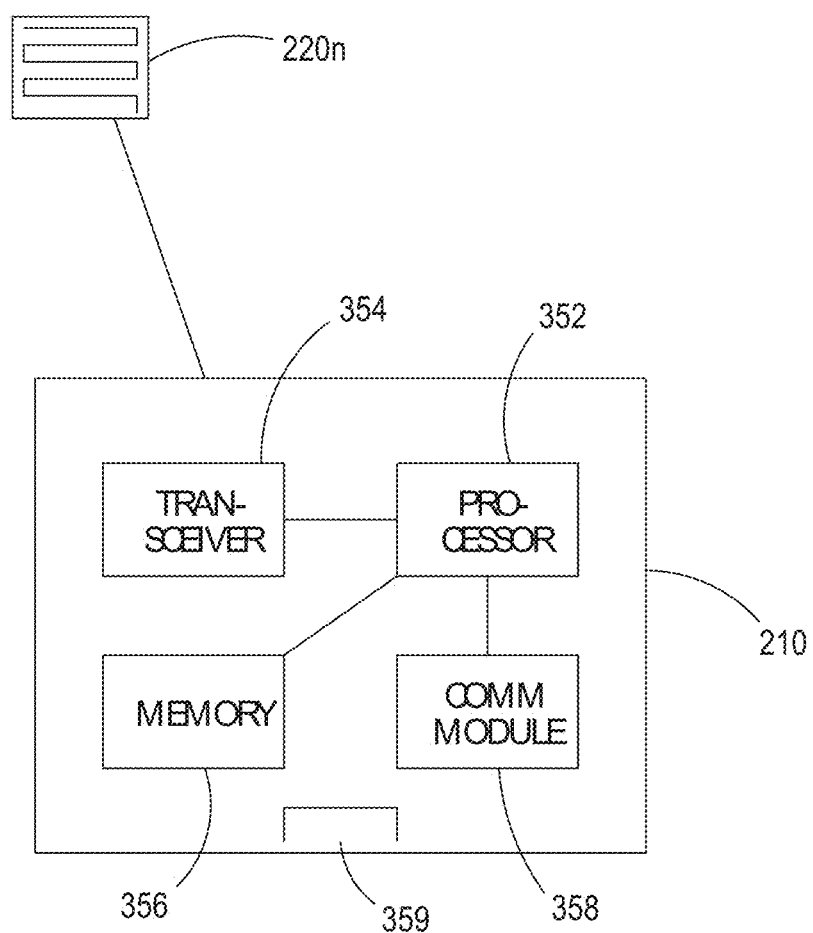
FIG. 3 illustrates a block diagram of an exemplary embodiment of a processing system for determining liquid content within a barrel in accordance with the principles of the invention.

FIG. 3 illustrates a block diagram of an exemplary embodiment of a processing system for determining liquid content within a barrel in accordance with the principles of the invention.

In accordance with the principles of the invention, processing system 210 comprises a transceiving (transmitter/receiver) system 354 that is in communication with antennas 220a . . . 220n (of which only antenna 220n is shown in FIG. 3). Transceiving system 354 may include one or more switching networks (not shown) that provide signals to selectively provide signals to a corresponding one of the plurality of antennas 220a, 220b, 220c . . . 220n. For example, transceiving system 354 may provide through a (not shown) switching network, signals to each of the plurality of antennas shown in FIG. 2, for example, in a sequential manner such that only one antenna is transmitting and/or receiving at any given time. Alternatively, the (not shown) switching network(s) may cause more than one antenna to concurrently transmit signals and/or receive reflection signals. Alternatively, the (not shown) switching network may cause at least one of the antennas to operate as a transmitting antenna while causing at least one of the plurality of antenna to operate as a receiving antenna.

Although element 354 is referred to as a transceiving system, it would be recognized that transceiving system 354 may comprise separate receiving and transmitting system without altering the scope of the invention claimed.

Processor 352 may comprise one or more conventional processing systems (e.g., INTEL Pentium serial processors) that operates to access instructions and provides control instruction to processing system 210. PENTIUM is a registered trademark of INTEL Corporation, a Delaware, USA corporation. Alternatively, processor 352 may comprise dedicated hardware and software that may provide control instruction to processing system 210.

Memory 356 provides storage capability for instructions (software, code) that may be accessed by processor 352 to control the processing of processing system 210. Memory 356 may for example be represented as semiconductor memory, such as a combination of PROM (programmable read-only memory), wherein instructions are permanently stored or RAM (random access memory), wherein data values may be accessed and overwritten.

Communication module (i.e., transmitter/receiver) 358 represents a means to provide data collected by processor 352 to one or more external devices (not shown), which may be used to evaluate, correlate and collate the data collected. Communication module 358 may comprise a wired or a wireless communication connection to the not shown external devices. For example, communication module 358 may be in wired communication with one or more systems that may be in communication with the Internet that allows for the monitoring of the determined fluid level over a broad geographical area.

Alternatively, communication module 358 may include elements that provide information through one or more wireless communication protocols (e.g., a very short-range NFC protocol (e.g., RFID), a short-range protocol (BLUETOOTH), a longer-range protocol (Wi-Fi) and a long-range protocol (e.g., cellular)). In addition, communication module 358 may operate to receive information from an external source either through a wired communication protocol or a wireless communication protocol. Such information may, for example, comprise instructions (code) that may be stored in memory 356, information regarding the tank (e.g., volume, dimensions, a type of material comprising the tank, etc.) to which system 150 is attached, and the content of the tank. This information may include information for the reprogramming, or the pairing, of system 150 with the specific tank (or barrel) 110. In one aspect of the invention, monitoring system 150 may be "paired" with a specific barrel, such that monitoring system 150 may monitor the contents of the paired barrel 110 over multiple uses of the barrel. For example, an identification number of the container (or barrel) to which monitoring system 150 is attached, may be input into memory 354. Alternatively, barrel 110 may include an electronic identification code that may be input via a wireless communication connection into monitoring system 150 (i.e., paired) using a short-range identification communication protocol (e.g., RFID).

Power source 359 provides power (electrical energy) to the electrical/electronic components of processing system 210. In one aspect of the invention power source 359 may represent a lithium-nickel battery that provides power to monitoring system 210 for an extended period of time. In another aspect of the invention, power source 359 may be a rechargeable battery element that may be recharged by removal from processing system 210 or recharged while included within processing system 210. Alternatively, power source 359 may be an AC to DC converter that receives electrical energy from a main source of power (e.g., 120-volt outlet) and converts the received power to a direct current that is used to power the electrical/electronic components of processing system 210.

Figure 4:
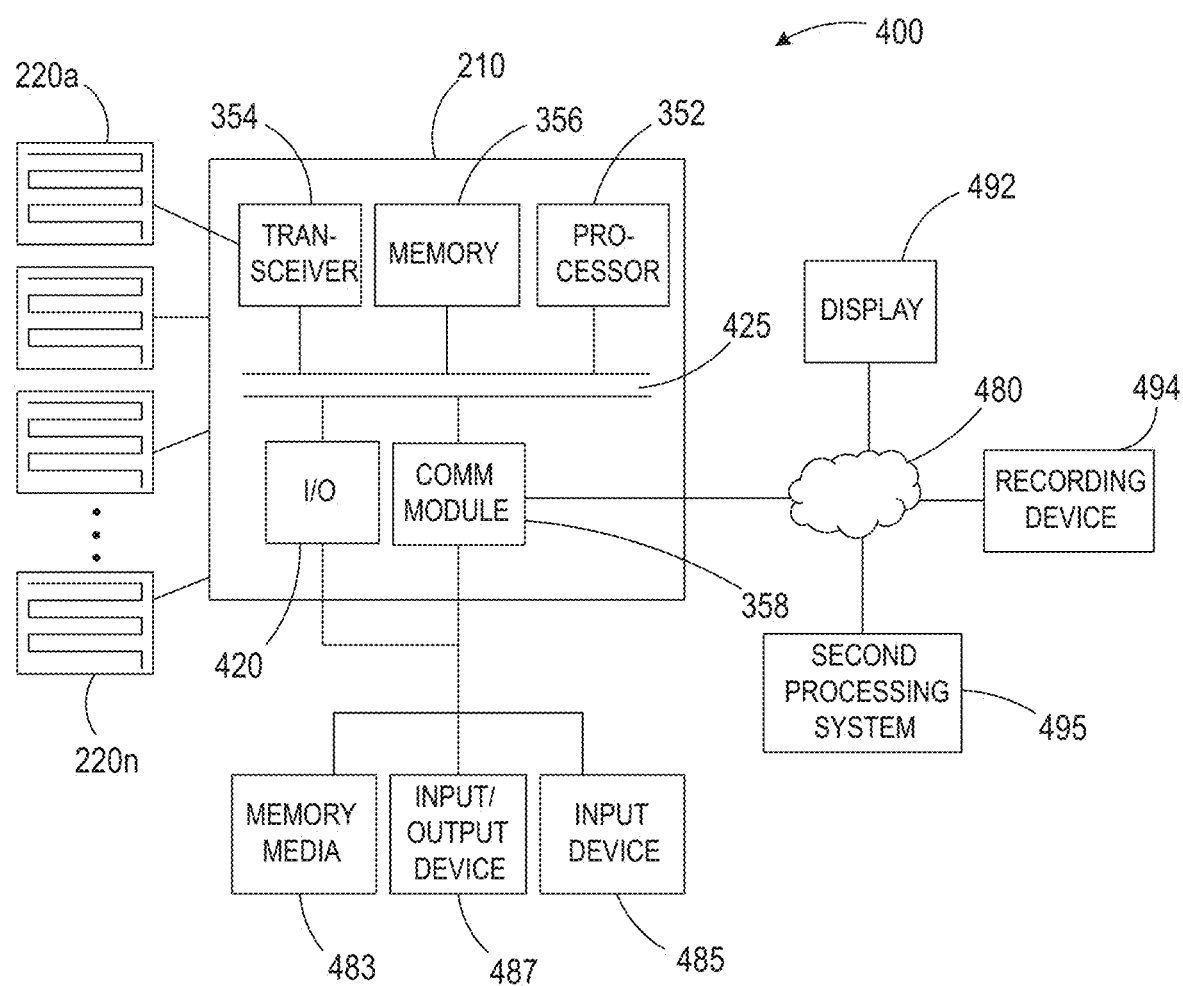
FIG. 4 illustrates a block diagram of an exemplary system for determining liquid content within a barrel in accordance with the principles of the invention.

FIG. 4 illustrates a block diagram of an exemplary system for determining liquid content within a barrel in accordance with the principles of the invention.

In this exemplary system embodiment 400, input data is received from antennas (sources) 220a . . . 220n and processed in accordance with one or more programs, either software or firmware, executed by processing system 210. The results of processing system 210 may then be transmitted over network 480 for viewing on display 492, reporting device 494 and/or a second processing system 495.

In the depicted implementation processing system 210 includes one or more receiving devices 354 that receive data from the illustrated sources or devices 220a . . . 220n. The received data is then applied to processor 352, which is in communication with input/output device 420 and memory 356. Transmitting/receiving element 354, processor 352 and memory 356 may communicate over a communication medium 425, which may represent a communication network, e.g., ISA, PCI, PCMCIA bus, one or more internal connections of a circuit, circuit card or other device, as well as portions and combinations of these and other communication media.

Processor 352 may be a general processor central processing unit (CPU) or a special purpose processing unit or dedicated hardware/software, such as a PAL, ASIC, FGPA, each of which is operable to execute computer instruction code or a combination of code and logical operations. In one embodiment, processor 352 may include, or access, software or code that, when executed by processor 352, performs the operations illustrated herein. As would be understood by those skilled in the art when a general-purpose computer (e.g., a CPU) loaded with or accesses software or code to implement the processing shown herein, the execution of the code transforms the general-purpose computer into a special purpose computer. The code may be contained in memory 356 or may be read or downloaded from one or more external devices.

For example, code or software may be downloaded from a memory medium, such as a solid-state memory or similar memory devices 483, or may be provided by a manual input device 485, such as a keyboard or a keypad entry, or may be read from a magnetic or optical medium (not shown) or via downloaded from a second I/O device 487 when needed. Information items provided by external devices 483, 485, 487 may be accessible to processor 352 through input/output device 420, as shown. Further, the data received by input/output device 420 may be immediately accessible by processor 352 or may be stored in memory 356. Processor 352 may further provide the results of the processing to one or more external devices (i.e., display 492, recording device 494 or a second processing unit 495).

As one skilled in the art would recognize, the terms processor, processing system, computer or computer system may represent one or more processing units in communication with one or more memory units and other devices, e.g., peripherals, connected electronically to and communicating with the at least one processing unit. Furthermore, the devices illustrated may be electronically connected to the one or more processing units via internal busses, e.g., serial, parallel, ISA bus, Micro Channel bus, PCI bus, PCMCIA bus, USB, etc., or one or more internal connections of a circuit, circuit card or other device, as well as portions and combinations of these and other communication media, or an external network, e.g., the Internet and Intranet. In other embodiments, hardware circuitry may be used in place of, or in combination with, software instructions to implement the invention. For example, the elements illustrated herein may also be implemented as discrete hardware elements or may be integrated into a single unit (e.g., ASIC).

As would be understood, the operations illustrated may be performed sequentially or in parallel using different processors to determine specific values. Processing system 210 may also be in two-way communication with each of the sources 220a . . . 220n. Processing system 210 may further receive or transmit data over one or more network connections 480 from a server or servers over, e.g., a global computer communications network such as the Internet, Intranet, a wide area network (WAN), a metropolitan area network (MAN), a local area network (LAN), a terrestrial broadcast system, a cable network, a satellite network (cellular), and a wireless network (Wi-Fi), as well as portions or combinations of these and other types of networks. As will be appreciated, network 480 may also be internal networks or one or more internal connections of a circuit, circuit card or other device, as well as portions and combinations of these and other communication media or an external network, e.g., the Internet and Intranet.

In one aspect of the invention, external devices 483, 485, 487, 492, 494, 495 may be representative of a handheld calculator, a special purpose or general-purpose processing system, a desktop computer, a laptop computer, tablet computer, or personal digital assistant (PDA) device, etc., as well as portions or combinations of these and other devices that can perform the operations illustrated.

Figure 5A:
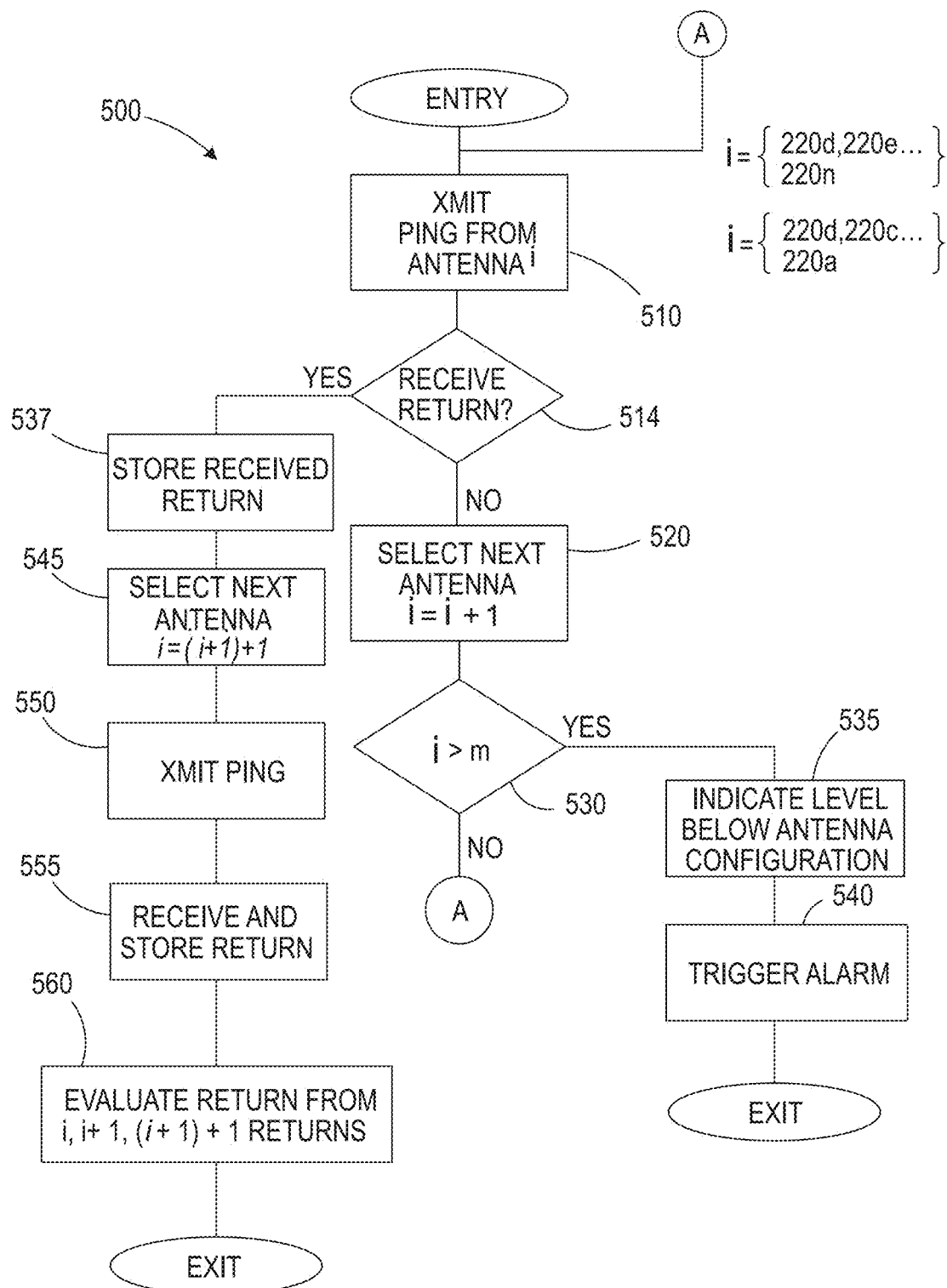
FIG. 5A illustrates a flowchart of an exemplary processing in accordance with the principles of the invention.

FIG. 5A illustrates a flowchart of an exemplary processing in accordance with the principles of the invention.

In this illustrated exemplary processing 500, the processing system 210 (described with reference to at least FIGS. 2-4) initiates transmission of a signal (referred to, hereinafter as "ping") to a selected one ("i") of the antenna 220a . . . 220n. In one aspect of the invention, the initially selected antenna may be selected as the top-most antenna (i.e., 220d, FIG. 2) as the container may be considered in an initially "full state."

In accordance with the illustrated embodiment shown in FIG. 2, processing may operate from the highest antenna 220d positioned on face 140 to the lowest antenna positioned on face 140 (220a or 220n). In one aspect of the invention, processing may select to operate with antennas selected from a first set of antennas (i.e., 220d, 220e . . . 220n—clockwise selection). Alternatively, processing may select to operate with antennas selected from a second set of antennas (i.e., 220d, 220c . . . 220a—counterclockwise selection). In still another alternative aspect of the invention, processing may select to operate using the first set of antennas and then the second set of antennas, wherein the first and second sets of antennas may be a symmetric or a non-symmetric relation with respect to a known point (e.g., center point 260). Although examples of the selection of the one or more antenna selected to be within the set of antenna are disclosed, it would be recognized that other methods of selection of antennas within the set of antenna may be implemented without altering the scope of the invention claimed.

Processing then selects, at step 510, an initial antenna selection, referred to as "i" from which a signal or a ping is to be transmitted. At step 514, processing waits for return or reflection of the transmitted ping.

Upon not receiving a return (or reflected) signal (after a known period of time, as discussed in FIG. 5B), processing continues to step 520, where a next ("i+1") antenna is selected from the selected clockwise or counterclockwise set of antennas. Processing then proceeds to step 530 where a check of the value (within the selected set) of the selected antenna is greater than the number of antenna (m) within the selected set of antenna. If the value of the selected antenna is greater than the number antenna within the set, then processing proceeds to step 535, wherein the returns (i.e., reflections of transmitted pings) from each of the antenna within the selected set of antenna is evaluated.

At step 535, the processing system 210 performs a test to determine if any return has been received from any antenna in the selected set. Upon determining no returns have been received from any of the antennas in the selected set, the processing system 210 sets an indication that no returns have been received from any of the antennas in the selected set and, hence, the liquid level is flagged as being "Too Low." At step 540, the processing system 210 triggers an alarm indication to indicate the "Too Low" condition.

Returning to step 530, if the value (within the selected set) of the next selected antenna is not greater than the number of antennas within the selected set, processing proceeds to step 510 to transmit (i.e., Xmit) a ping from the selected (next) antenna.

Returning to step 514, when a return is detected, processing proceeds to step 537 where the received return is stored. At step 545, a next antenna is selected ((i+1)+1), wherein processing proceeds to step 550 to transmit a ping from the selected (next) antenna. At step 555, a return from the transmitted "ping" is received and subsequently stored.

At step 560, the returns from the i, i+1 and (i+1)+1 antenna selected are evaluated to determine a level of the contained liquid.

As the antenna selection is made from highest to lowest antenna placement on face 140 (in this illustrative processing) after two sequential returns are received, processing is halted as each of the antennas lower in position to the (I+1)+1 antenna would be in contact with the contained liquid and, thus, information from these lower antennas do not contribute any additional information to the level of the contained liquid. This limitation of the number of antennas transmitting is advantageous as it reduces the power requirements needed in obtaining a level of the contained fluid.

Although FIG. 5A refers to processing for selecting one antenna in one of a clockwise set and a counterclockwise set of antennas, it would be understood that the processing shown in FIG. 5A may be adaptable to select first one set of antennas (e.g., clockwise) and then select the other set of antennas (e.g., counterclockwise) to determine the level of the contained liquid.

In one aspect of the invention, wherein the position of the antennas within one set (e.g., clockwise) of antenna on face 140 may be spatially offset from a position of the antenna in the second set (e.g., counterclockwise) of antenna on face 140 (i.e., non-symmetrical relation), the use of information from both the first and second sets of antenna provides for a more precise determination of the liquid within container 110.

Figure 5B:
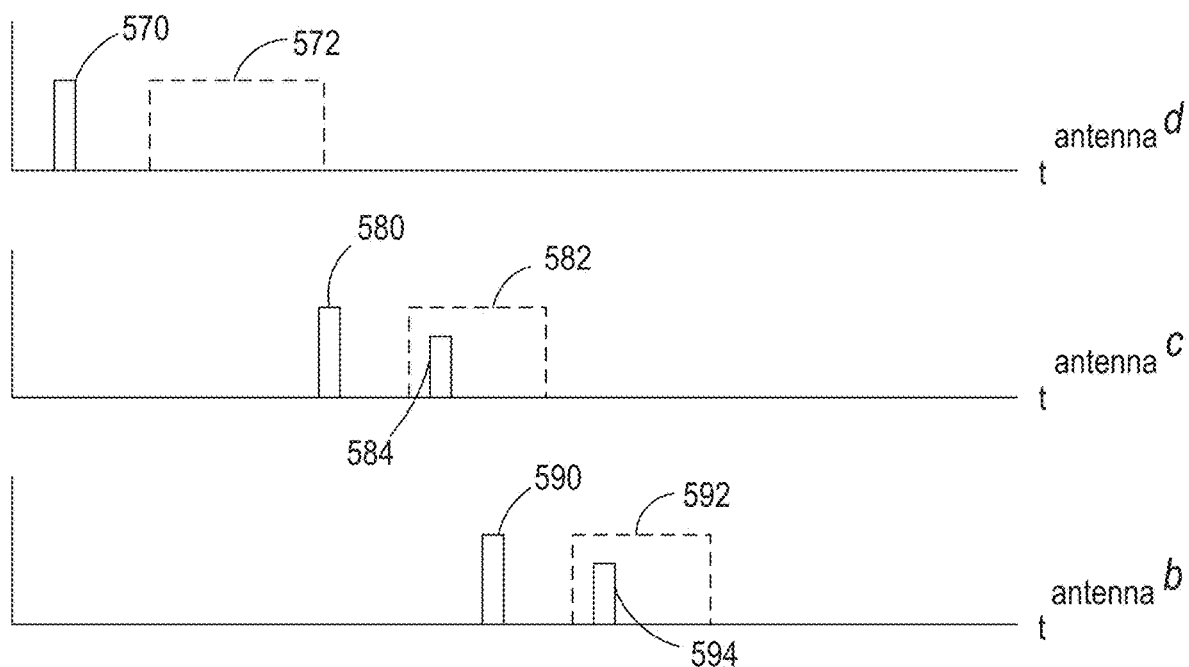
FIG. 5B illustrates an exemplary timing chart in accordance with the principles of the invention.

FIG. 5B illustrates an exemplary timing chart in accordance with the principles of the invention.

In this illustrated example, which corresponds to the processing shown in FIG. 5A, an initial ping or transmission 570 is made from antenna 220d (the highest antenna illustrated in FIG. 2). A return window 572 is opened. The time period the return window 572 remains open is based on the expected time of the detection of a return to ping 570.

In this illustrated example, a return is not detected within the expected time, which is flagged as a return, but a NO response. Processing proceeds to select a next antenna (e.g., antenna 220c), wherein a ping 580 is transmitted and a return window 582 is opened. In this illustrated example, return 584 is detected and window 582 is closed. A next antenna (e.g., antenna 220b) is selected from which ping 590 is transmitted and return window 592 is opened.

As illustrated, return 594 is detected and, thus, window 594 is closed.

Figure 6:
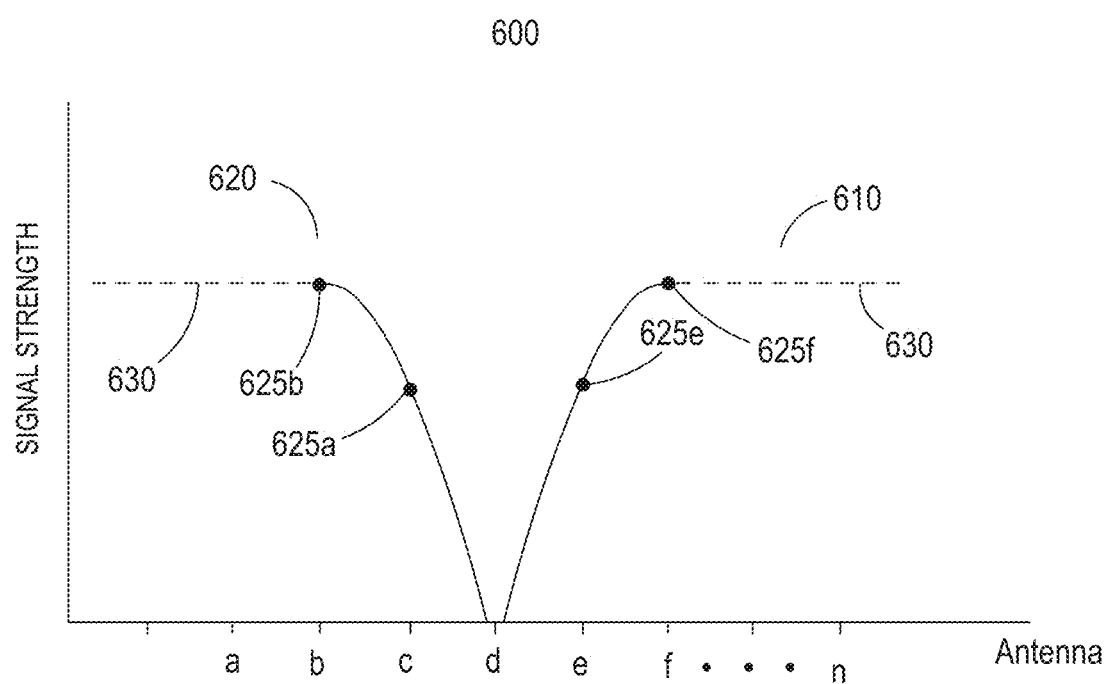
FIG. 6 illustrates a graph of an exemplary signal return chart for determined liquid content within a barrel in accordance with the principles of the invention.

FIG. 6 illustrates a graph of an exemplary signal return chart 600 for determining liquid content within a barrel in accordance with the principles of the invention.

In this illustrated example, which is related to the timing diagram shown in FIG. 5B, the transmission of a ping from antenna 220d produces no return and, hence, no signal is shown for antenna 220d in FIG. 6. However, with the selection of antenna 220e and 220f, returns 625e and 625f detected by antenna 220 and 220f, respectively are shown on graph segment 610.

With the detection of return 625e and, a second (confirmation) return 625f, processing may be halted and a level of contained liquid may be determined.

Further illustrated are returns 625c and 625b, associated with antenna 220c and 220b, (see FIG. 2), respectively on graph segment 620.

In accordance with one aspect of the invention, returns 625b, 625c, 625e and 625f may be evaluated (e.g., signal strength) to determine a level of the contained fluid.

In accordance with another aspect of the invention, the position of antennas 220b, 220c may be spatially offset (i.e., physically displaced) from antennas 220e, 220f and, thus, the evaluation of the received returns may determine the level of the contained liquid more precisely, as previously discussed.

Figure 7A:
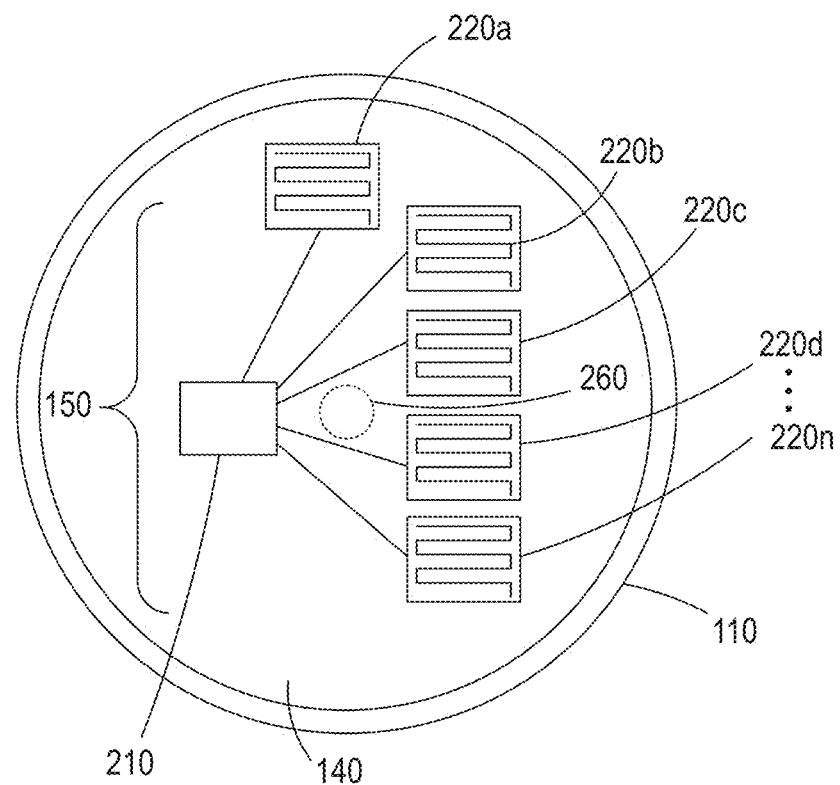
FIGS. 7A and 7B illustrate a first and second aspect of a second exemplary embodiment of a system for determining liquid content within a barrel in accordance with the principles of the invention.

FIG. 7A illustrates a first aspect of a second exemplary embodiment of a system for determining liquid content within a barrel in accordance with the principles of the invention.

In this illustrated configuration, antenna 220a, 220b . . . 220n are arranged linearly on face 140 of barrel 110.

In this illustrated configuration, antenna 220a, 220b, 220c, . . . 220n are shown in a linear arrangement, wherein processing similar to that shown in FIGS. 5A, 5B and 6 may be performed.

Figure 7B:
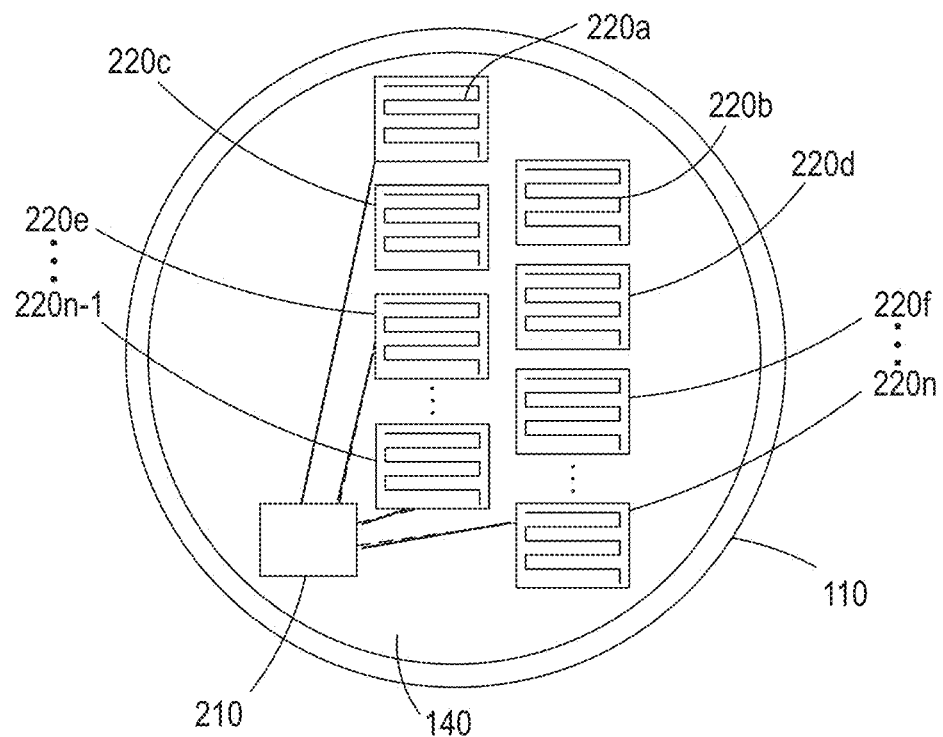

FIG. 7B illustrates a second aspect of a second exemplary embodiment of a system for determining liquid content within a container (or barrel) in accordance with the principles of the invention.

In this illustrated configuration, antenna 220a, 220c . . . 220n–1 may be arranged in a first set and antenna 220b, 220d . . . 220n may be arranged in a second set of antennas that is spatially offset from the first set of antennas. As discussed with regard to FIG. 2, the positioning of the illustrated plurality of antenna in a physically non-symmetrical relation allows for a more precise determination of a level of fluid within barrel 110. In the implementation depicted by FIG. 7A the processing system 210 is disposed at a known offset distance from the center point 260 of the face 140 of the barrel 110. The implementation depicted by FIG. 7B includes but does not show the barrel 110 face 140 center point 260 that is not visible behind the depicted antenna 220e.

Accordingly, a determination of the level of a contained liquid may be made based on the receiving of reflections of transmitted pings or signals as previously discussed.

Figure 8:
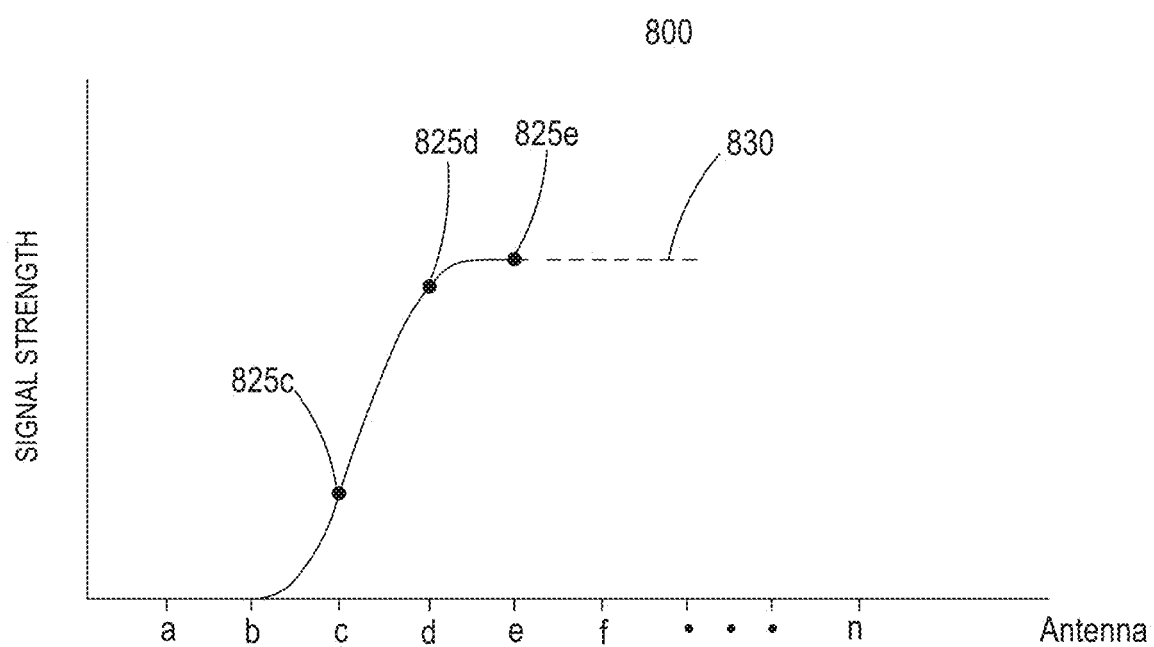
FIG. 8 illustrates a graph of an exemplary signal return chart associated with the configurations shown in FIGS. 7A and 7B for determined liquid content within a barrel in accordance with the principles of the invention.

FIG. 8 illustrates a graph of an exemplary signal return chart 800 associated with the configurations shown in FIGS. 7A and 7B in accordance with the principles of the invention.

In accordance with this aspect of the invention, signals transmitted by antenna 220a, 220b (two physically highest antenna, FIGS. 7A and 7B) fail to provide a response within an expected time window (FIG. 5B) and, thus, a first return 825c is received from the transmission of a ping from antenna 220c with a subsequent return 825d received from the transmission of a ping from antenna 220d as shown on graph segment 830. As discussed previously, processing may be halted after two consecutive returns are received.

In accordance with one aspect of the invention, when the returned signal level differ by a known amount, a next transmission and return 825e may be executed to validate a previous return (e.g., 825d)

In this illustrative example, a level of the content liquid in barrel 110 may be determined as lying between the position of antenna 220b and 220c, based on the strength of return signals depicted by FIG. 8. Hence, with the knowledge of the position of each of the antenna with respect to center point 260 (FIG. 2), the level of liquid 120, and the volume content within barrel 110 may be accurately determined.

Figure 9:
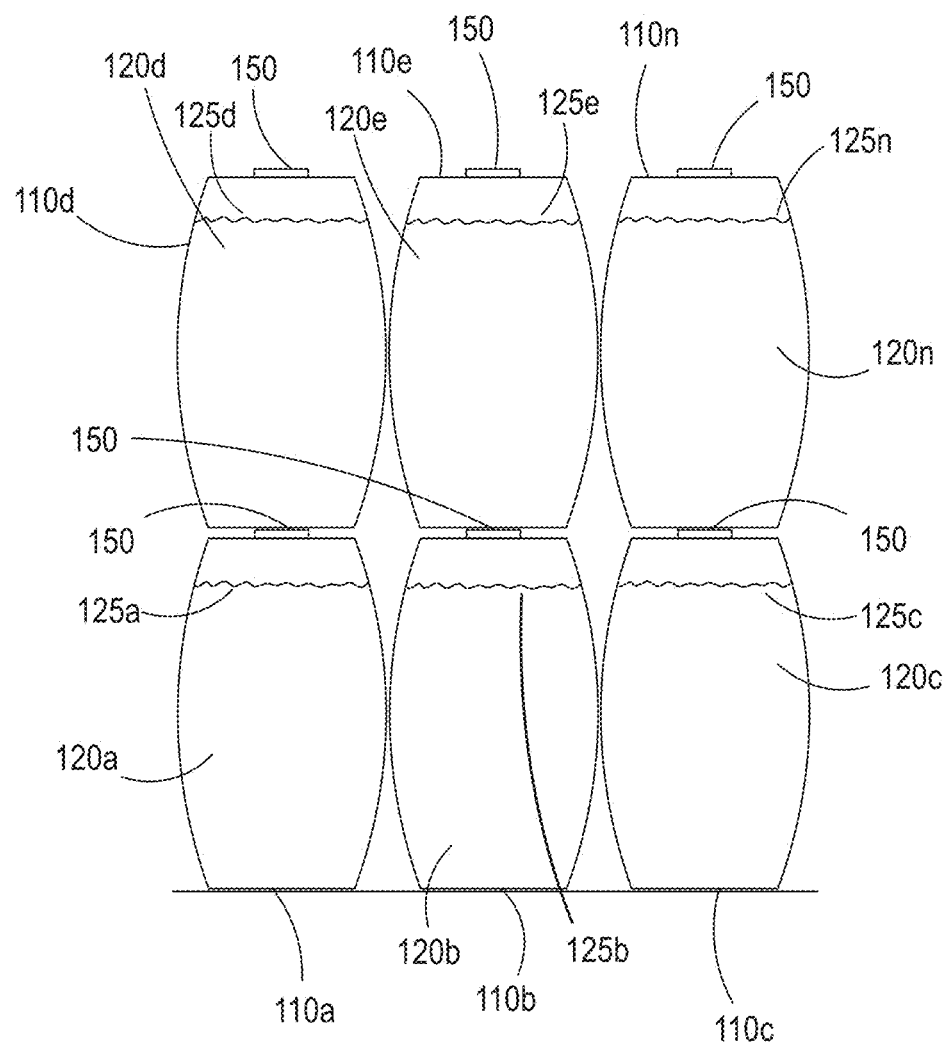
FIG. 9 illustrates a second conventional configuration for storing a plurality of barrels and the liquid contained therein.

FIG. 9 illustrates a second conventional configuration for storing a plurality of barrels and the liquid contained therein.

In this second configuration of storing barrels, barrels 110a, 110b, . . . 110n are stored vertically where monitoring system 150 is attached to face 140 of each of the illustrated barrels 110. The implementation depicted by FIG. 9 shows the exemplary respective liquid levels 125d, 125e, 125n, 125a, 125b, 125c of liquids 120d, 120e, 120n, 120a, 120b, 120c.

In this illustrated configuration, it would be recognized by those skilled in the art that the level of the contained liquid with each of the barrels may be obtained from a single signal or ping, as the level of the liquid is measured from face 140.

Accordingly, monitoring system 150 may be configurated to include a single antenna configuration that may be used to monitor the vertically displaced liquid within the vertically stacked container(s) 110.

Figure 10:
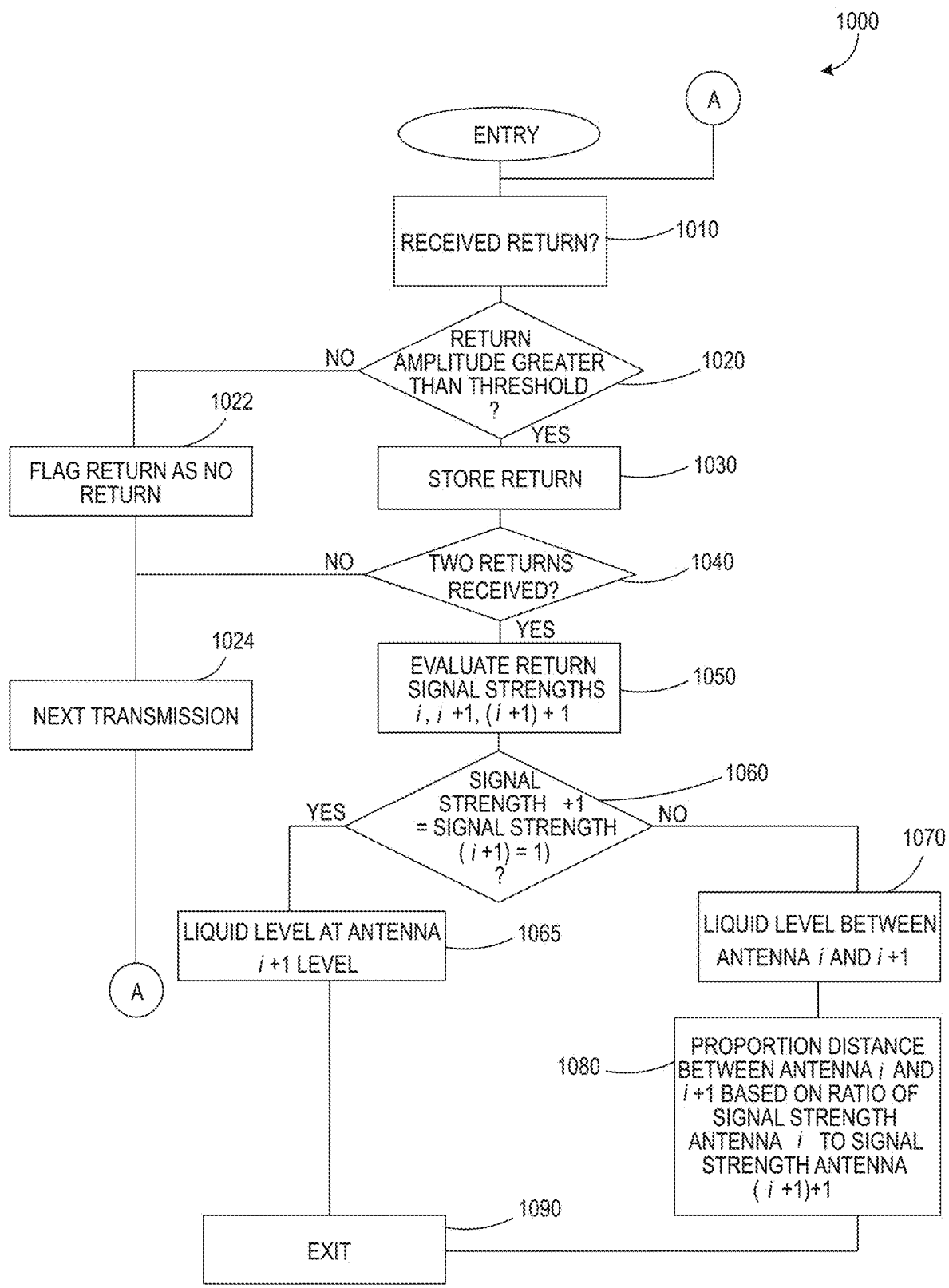
FIG. 10 illustrates a flowchart of an exemplary processing for determining liquid content within a barrel in accordance with the principles of the invention.

FIG. 10 illustrates a flowchart of an exemplary processing for evaluating the return signals in accordance with the principles of the invention.

In accordance with the illustrated processing 1000, a determination is made at step 1010 as to whether a return has been received. If so, a signal strength or amplitude of the received signal (i.e., the return) is evaluated with regard to a threshold level at step 1020. If the received signal strength is less than or equal to a predetermined minimum threshold level, then processing continues to step 1022, where the return is removed from the processing and an indication of NO return is associated with the transmitted ping. At step 1024, a next antenna is selected (as previously discussed) and processing continues at step 1010.

Returning to step 1020, if the return signal strength is greater than the predetermined minimum threshold, then processing proceeds to step 1030 where the return is stored.

At step 1040 a determination is made whether two consecutive returns have been received. If not, then processing proceeds to step 1024, wherein a next transmission is initiated.

However, if two consecutive returns have been received, the processing continues to step 1050 to evaluate the received signal strengths associated with the first return (i.e., antenna i+1) and the second return (i.e., antenna i+1+1).

At step 1060 a determination is made whether the received signal strengths of the two consecutive returns are approximately the same. If so then the contained liquid level is determined to be comparable to the position of the i+1 antenna at step 1065. Processing then proceeds to step 1090 where the processing is ended.

Returning to step 1060, if the signal strengths are not approximately equal, then the liquid level may be determined to be between the i$^{th}$ and the i$^{th}$+1 antenna at step 1070. In one aspect of the invention, the liquid level may be determined proportionally between the i$^{th}$ and the i$^{th}$+1 antenna based on the signal strength of the i$^{th}$+1 antenna with respect to the signal strength of the i$^{th}$+1+1 antenna.

Processing then proceeds to step 1090 to exit.

In accordance with the principles of the invention, the determined level of the contained liquid, based on the signal strength of at least two responses or reflections, which are greater than a threshold value, may then be transmitted to one or more of the illustrated external devices shown in FIG. 4. In one aspect of the invention, threshold value may be preset within memory 356. Alternatively, a threshold value may be downloaded into memory 356 in a manner as previously discussed. In still another aspect of the invention, the threshold value may be dynamically determined, based in part, on the characteristics of the container. For example, a size of the container, a material of the container, etc. For example, a calibration of the monitoring system 150 may occur once placed on a face 140 of a container, wherein the characteristics of the container and/or contained liquid may be entered into monitoring system 150. A series of transmissions may occur from one or more of antenna 220a . . . 220n, and the responses to the series of transmissions may be evaluated for establishing a threshold value that enables signals that may be considered valid responses to the processed.

In one aspect of the invention, a volume of the contained liquid may be obtained from at least the determined fluid level and knowledge of the physical dimensions of the container. For example, the volume of the barrel or tank may be determined as:

$$V(tank)=\pi r^2 L$$

where L is the length of the tank; and
r is the radius of a circular segment of the tank The filled volume of a horizontally oriented tank or barrel, for example, may be determined by first finding an area, A, of a circular segment and multiplying it by the length, L.

A partial volume calculation may next be derived as:

$$A = (1/2)r 2(\Theta - \sin\Theta)$$

where $\Theta = 2*\arc\cos(m/r)$ and
$\Theta$ is in radians.

Accordingly, a volume of a segment may be determined as:

$$V(\text{segment}) = (1/2)r^2(\Theta - \sin\Theta)L.$$

If the determined fluid level, f, is less than ½ of "d", then the segment created from the level height and V(fill)=V (segment).

However, if the fluid level, f, is greater than ½ of "d" then, the segment that is created by the empty portion of the tank may be determined and subtracted from the total volume of the container or tank to obtain:

$$V(\text{fill}) = V(\text{tank}) - V(\text{segment}).$$

In another aspect of the invention, for vertically oriented barrels, the volume of the contained liquid may be obtained as:

$$V(tank)=\pi r^2 h,$$

where h is height of the contained fluid.

FIGS. 11A-11C illustrate exemplary signal transmission and signal return graphs as a function of time in accordance with a further aspect of the invention.

In accordance with this further aspect of the invention, the quality of a container may be determined by the long-term evaluation of the losses (leakage and/or absorption) of the liquids contained with the container. The long-term evaluation of the losses associated with a container may further be utilized to determine a rate of testing of the liquid within the container.

FIG. 11A illustrates an exemplary signal transmission graph 1100 as a function of time, wherein signal transmissions occur within bursts over an extended period of time. In accordance with the principles of the invention, the duration of the usage of monitoring system 150 is divided into a plurality of periods 1106, 1107, 1108, 1109, 111, 1113 and 1117, which are referred to in this exemplary illustration as collection time periods. Further shown are a plurality of transmission bursts 1105, 1110, 1115 . . . 1150, wherein a measurement of a fluid within a container is made.

FIG. 11B is an expanded view of burst 1105, which is identified as FIG. 11B in FIG. 11A.

In this illustrated example, a plurality of transmissions 570, 580 and 590 (which are comparable to the transmissions shown in FIG. 5B) are included within burst 1105, wherein the plurality of transmissions are associated with at least one of the illustrated antenna 220a-220n, as previously discussed. Accordingly, a collection of fluid levels may be obtained for each of the illustrated transmission bursts.

In one aspect of the invention, processing system 210 may include a timer circuit (not shown) that provides an alarm clock feature that causes processing system 210 to transmit burst 1105, containing transmissions 570, 580, 590. After processing the associated reflections from transmissions 570, 580, 590, processing system 210 may enter a sleep mode, in which little power is consumed. After burst 1105 is completed, processing system 210 may again be activated by the timer circuit (not shown) to cause the transmission of signals (i.e., 570, 580, 590) within burst 1110.

This process of sleeping after each burst is completed and activating after a known time thereafter (e.g., 1112, 1114, 1119, 1124 . . . 1149) repeats for the life of the container or barrel to which monitoring system 150 is attached.

This process of sleeping and activation is advantageous as it provides for extended usable life of a fixed, or dedicated power source.

In one aspect of the invention, the activation time may be substantially constant such that fluid measurement may be made at a known rate. For example, burst transmissions 1105 . . . 1150 may occur at a known rate (e.g., a daily basis, a weekly basis, a monthly basis, etc.). The desired rate of fluid measurement may be input into processing system 210 as previously described.

Alternatively, and as shown in FIG. 11A, the rate of fluid measurement may be made dynamically, based on changes in the fluid measurement over time.

FIG. 11C illustrates an exemplary graph 1140 of corresponding fluid levels or container volume determined based on the return signals associated with the transmission bursts.

In this exemplary graph, a fluid level or container volume value 1155 may be determined based on the signal transmissions/signal returns associated with burst 1105. Similarly, a fluid level or container volume value 1160 may be determined based on the signal transmissions/signal returns associated with burst 1110. And in accordance with the principles of the invention, fluid levels or container volumes 1165, 110, 1175, 1180 1185, 1195, etc. may be determined based on the signal transmissions/signal returns associated with corresponding transmission bursts 1115, 1120, 1125, 1130, 1135, 1150, etc.

As illustrated, the determined fluid level, or volume, initially decreases from a high value 1155 (i.e., full barrel) to a lower value 1175 and then remains substantially constant (i.e., 1175, 1180, 1185) as the losses from leakage and/or absorption decrease over time.

Accordingly, the rate of change of the fluid level or volume may, thus, be used to determine a duration of a sleep state of processing system 210. For example, when the rate of change of the fluid level is high (e.g., level 1155 to level 1160), signal transmission bursts and subsequent level measurements may be performed at a first rate (e.g., once/day). However, as the rate of change of the measured fluid level is slowing (e.g., level 1165 to level 1170) the duration of a sleep state of processing system 210 may be increased such that signal transmission bursts and measurements are performed at a second rate (e.g., once/week). In addition, as the rate of change of the measured fluid level is determined to be substantially negligible (e.g., level 1180 to level 1185) the duration of the sleep state of processing system 210 may be increased still further.

This dynamic determination of the rate of measurement is further advantageous as it further decreases the power needed to maintain system 150 for extended periods (e.g., multiple years).

Figure 12:
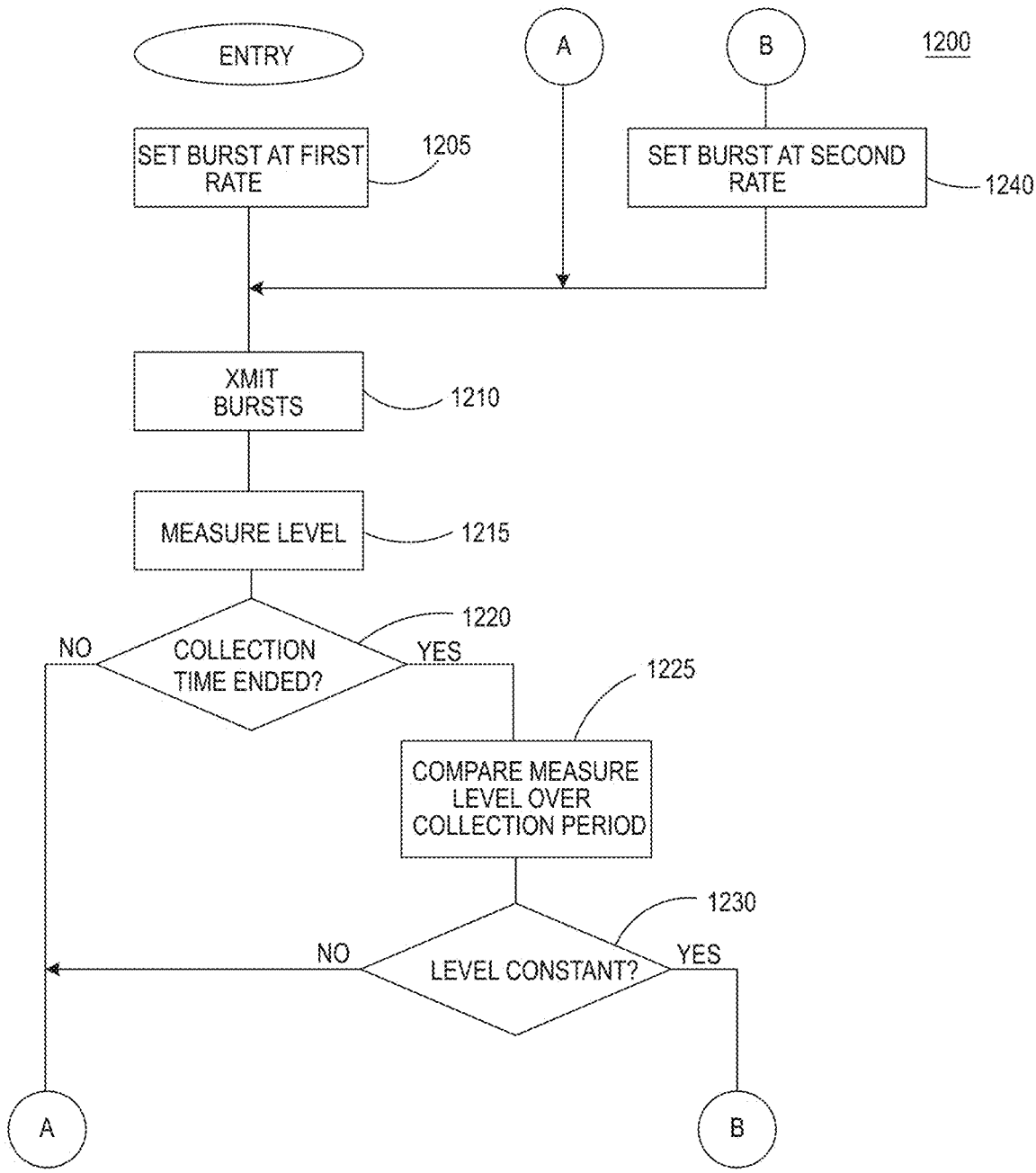
FIG. 12 illustrates an exemplary processing associated with the graphs shown in FIGS. 11A and 11B.

FIG. 12 illustrates an exemplary processing 1200 associated with the graphs shown in FIGS. 11A-11C.

In this illustrated process, the rate of burst transmission 1105-1150 (each containing signal transmission 570, 580 590) is set to a first rate at step 1205. At step 1210, a burst transmission (e.g., 1105) occurs wherein a fluid level (or volume) is determined at step 1215, as previously discussed. At step 1220, a determination is made whether a collection time has ended. If not, then processing proceeds to step 1210 to cause the emission of a second or next burst transmission (e.g., 1110), wherein a second measurement level is determined. At step 1220, a determination is again made as to whether a collection time has ended (e.g., 1106).

If the collection time has ended, processing proceeds to step 1225, wherein the determined fluid level (volume) (e.g., 1155, 1160) are evaluated to determine a rate of change of the determined fluid levels.

At step 1230, a determination is made whether the rate of change is small (i.e., substantially constant level). If the rate of change is not small (i.e., fluid level is not substantially constant) then processing proceeds to step 1210, wherein a next set of burst transmission (e.g., 1115, 1120) occur at the first rate.

However, if the rate of change of the fluid level is small (i.e., fluid level is determined to be substantially constant), then processing proceeds to step 1240, wherein the rate of subsequent transmission bursts is set to a second rate. As shown in FIG. 11A, the second rate is increased such that processing system 210 remains in a sleep state for a longer period and a lesser number of burst transmissions 1130, 1135 occur in an associated collection time period.

To further provide valuable information to the distillers, a measure of alcohol content of the remaining fluid may be determined from the determined evaporation/absorption of the fluid or liquid within the container.

Distilled liquids are stored in warehouses that are generally not climate controlled, and, hence, the ambient or surrounding environment affects the rate of evaporation and/or absorption of the contained liquids.

Environmental factors, such as temperature, barrel characteristics, time and geography contribute to a rate of change of an alcohol content of the fermenting liquid or fluid within a container. Local climate, which includes temperature, temperature fluctuations, and humidity, also affects the rate of evaporation. Local geography, such as altitude, seasonal variations and air quality also affects the rate of evaporation, and, consequently, the alcohol content within the barrel. In addition, the condition of the container is also a factor in the rate of production of alcohol in the container.

Figure 13:
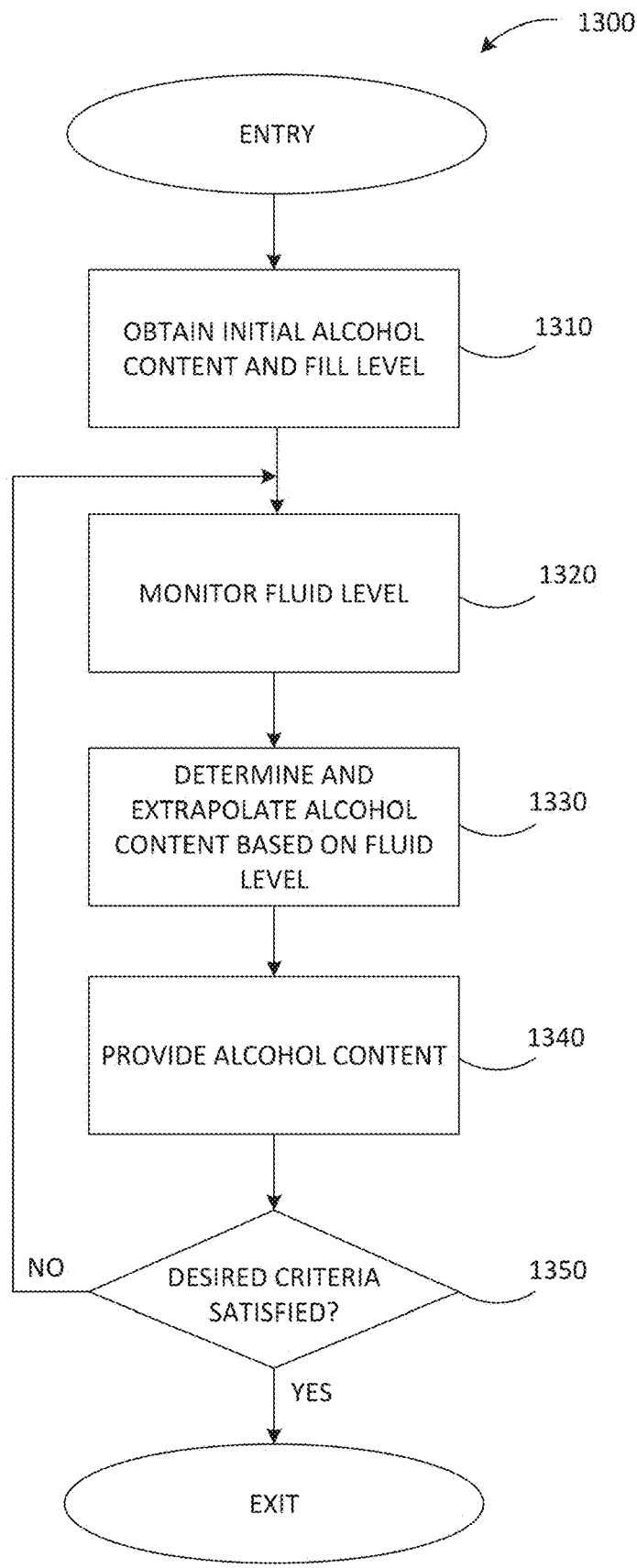
FIG. 13 illustrates a flowchart of an exemplary process associated with a determination of an alcohol content within a container in accordance with the principles of the invention.

FIG. 13 illustrates an exemplary process for determining alcohol content of a fermenting fluid within a container in accordance with the principles of the invention.

In this illustrated exemplary process 1300 upon filling a barrel or container with a liquid that is to be fermented, a measure of an initial alcohol content is determined and stored at step 1310. For example, the liquid entered into the container or barrel represents a mash that has been obtained from a distillation process associated with the fermentation of a base material, such as barley, rye, corn, wheat or a combination thereof.

At step 1320, a measure of the fluid level within the container is made. The measure of fluid level may be determined continuously, periodically or intermittently, utilizing one or more of the methods previously discussed.

At step 1330, a determination of an alcohol content is performed based at least on a determined fluid level and one or more environmental factors. At step 1340, the determined alcohol content is presented to a user for evaluation.

At step 1350 a determination is made whether one or more criterion associated with a desired requirement is satisfied. For example, determined alcohol content is within a desired range and/or a minimum length of time of the aging of the liquid within the container has been exceeded.

If one or more criterion is not satisfied, processing proceeds to step 1320 for further continued monitoring of fluid level and evaluation of alcohol content. As previously discussed, the monitor of the fluid level (and evaluation of alcohol content) may be determined periodically or continuously. In one aspect of the invention, the period of sampling may be based on a duration of time the liquid is within the barrel. That is, the interval between sampling is shorter during the early stages of fermentation and longer as the period of fermentation is increased.

Otherwise, processing is ended.

Figure 14:
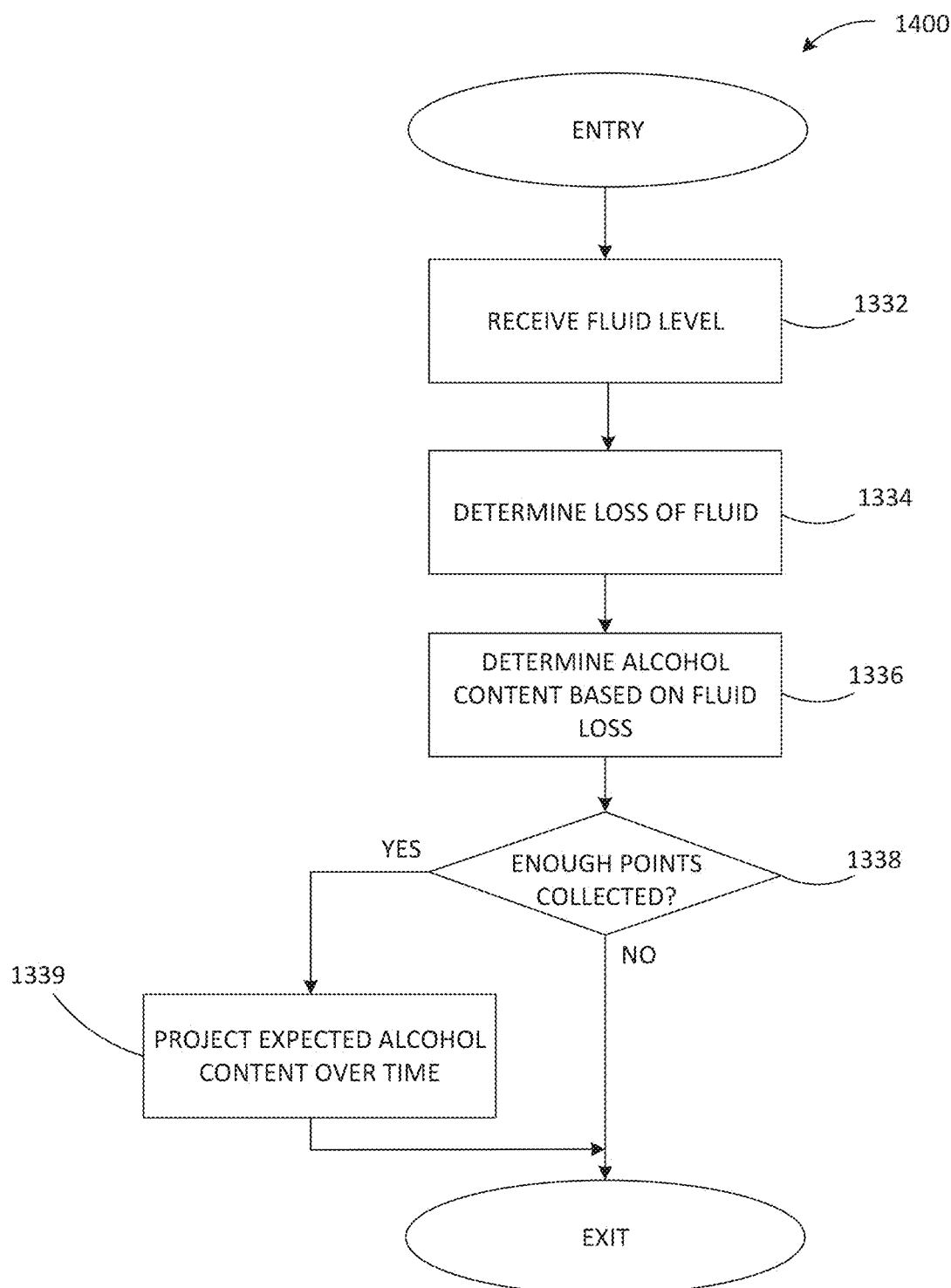
FIG. 14 illustrates a flowchart of an exemplary process for determining and extrapolating alcohol content of a liquid within a container in accordance with the principles of the invention.

FIG. 14 illustrates a flow chart of an exemplary processing associated with step 1330 of FIG. 13 for determining and extrapolating alcohol content of a liquid within a container in accordance with the principles of the invention.

In this exemplary process 1400, processing receives at step 1332 a fluid level obtained from a monitoring system, as previously discussed. At step 1334, a determination of a loss of fluid or liquid is determined, wherein the loss of fluid may be due to evaporation of the fluid or absorption of the fluid by the container as the container remains in place over an extended period of time.

At step 1336, an alcohol content of the liquid or fluid remaining in the container is determined, wherein the alcohol content is determined based, in part, on the at least one of an initial alcohol content, and one or more environmental conditions.

At step 1338 a determination is made as to whether enough data points have been collected. If enough data points have been collected, a determination of an expected alcohol content (i.e., a projection of alcohol content) is performed at step 1339. For example, and as would be known in the art, when two data points are collected, a straight-line approximation of the alcohol content may be obtained. In an illustrative example, when three data points are collected, a curved line, passing through the collected points, may be formulated that provides for an approximation of the expected alcohol content. When additional sample points are collected a more accurate approximation of the expected alcohol content may be obtained. In one aspect of the invention, at least three data or samples points are to be collected to obtain a first order approximation of the expected alcohol content. In another aspect of the invention, the process of determining an approximation of the expected alcohol content is performed as a selected number (e.g., a specified subset, or all) of the data points collected so as to obtain a more accurate approximation of the expected alcohol content.

Otherwise, processing exits.

Figure 15:
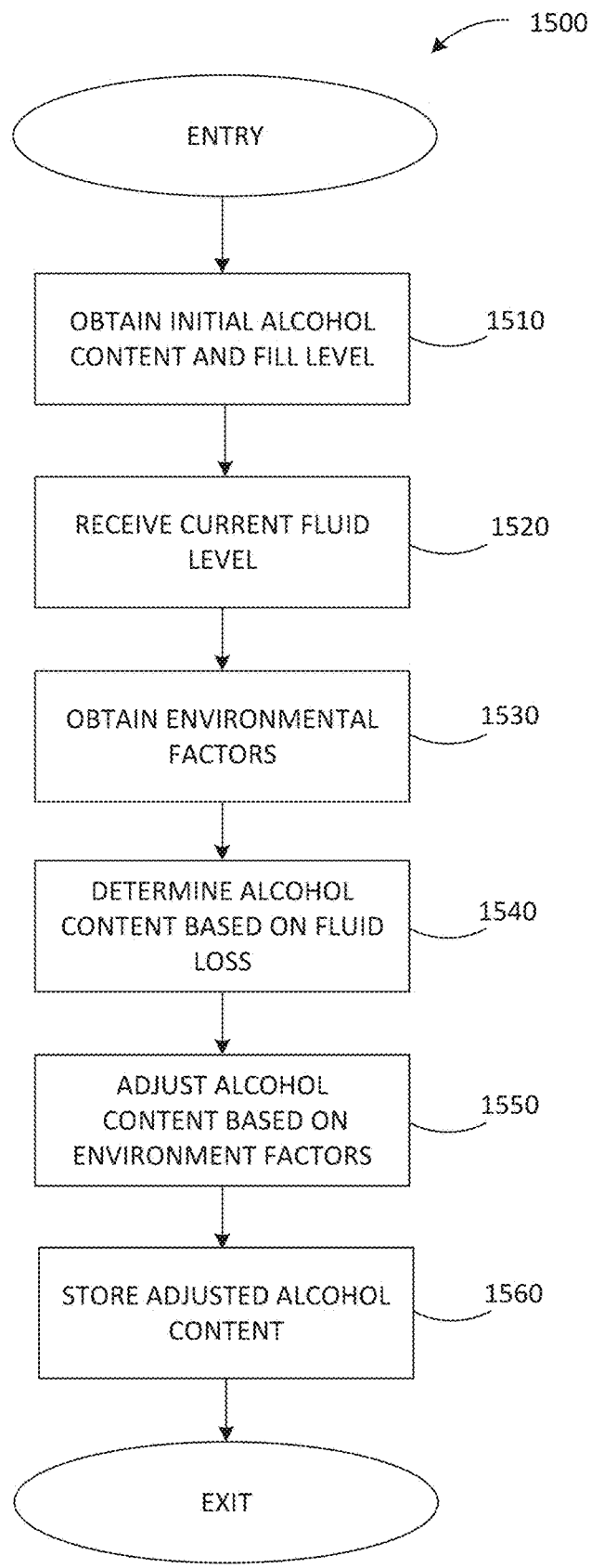
FIG. 15 illustrates a flowchart of an exemplary process for determining alcohol content of a liquid within a container in accordance with the principles of the invention.

FIG. 15 illustrates a flowchart of an exemplary process associated with step 1336 of FIG. 14 for determining alcohol content of a liquid within a container in accordance with the principles of the invention.

In the illustrated process, an initial alcohol content and fill level are obtained at step 1510. At step 1520, a determination of a loss in liquid or fluid level is based on the initial fill level and the determined current fill level. At step 1530, environmental factors surrounding the container are obtained. These factors may include information regarding temperature, humidity, seasonal variations, etc.

At step 1540 a determination of a current alcohol content is determined from the determined loss, wherein a nominal alcohol content decrease (or increase) is utilized to determine the current alcohol content. In one aspect of the invention, the nominal alcohol content decrease or increase is substantially constant over time. In another aspect of the invention, the nominal alcohol content increase or decrease may be variable, wherein the nominal alcohol content increase or decrease varies over time. In one aspect of the invention, the alcohol content may be determined based on a model of alcohol content over time, wherein the model may be developed by a series of actual measurements obtained over a known time period.

At step 1550 the determined alcohol content is subjected to a process for adjusting the determined alcohol content based on environment factors. And at step 1560, the adjusted alcohol content is stored for subsequent processing.

Figure 16:
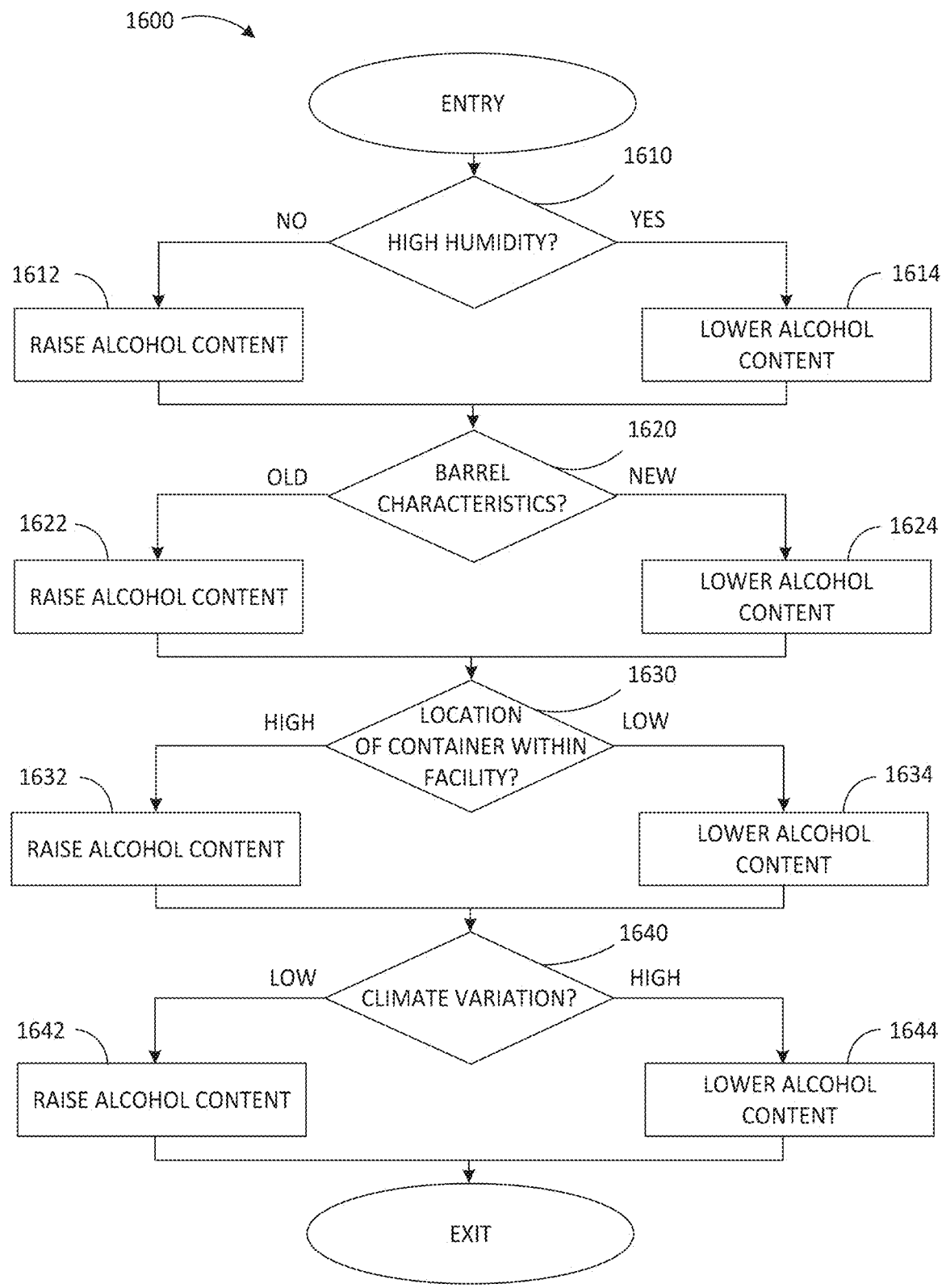
FIG. 16 illustrates a flowchart of an exemplary process for adjusting a determined alcohol content based on environmental considerations.

FIG. 16 illustrates a flowchart of an exemplary process associated with adjusting alcohol content presented in step 1550 based on one or more environmental factors or considerations.

In accordance with this exemplary processing 1600, at step 1610, a determination is made regarding the humidity level in the surrounding environment. If it is determined that the humidity level is high, then the alcohol content is lowered, at step 1614, as alcohol evaporates more quickly in high humidity conditions than water. In an illustrative example, a threshold humidity level of fifty percent may be considered as a high humidity level. The threshold humidity level may be adjusted in accordance with what would be known to one of ordinary skill. Otherwise, the alcohol content is raised at step 1612. The degree of raising or lowering the alcohol content may be constant. Alternatively, the degree of raising or lowering the alcohol content may be varied based on the level of humidity. In still another aspect, the degree of raising or lowering the alcohol content may be varied based on a length of time the contained fluid or liquid has been subjected to the humidity conditions.

At step 1620, a determination is made regarding the condition of the container. If it is determined that the container is essentially new, or has been used a few times, then processing proceeds to step 1624 where the alcohol content is lowered, as a newer container affords greater absorption of the contained fluid. Otherwise, at step 1622 the alcohol content is raised, as there is less absorption of the contained fluid.

At step 1630, a determination is made regarding a location of the container. For example, a determination of a high position within a stack of containers may require a raising of the alcohol content, at step 1632 as the higher position may cause greater temperature fluctuations around the container. Otherwise, the alcohol content may be lowered at step 1634 as it is expected that less temperature fluctuation exists around the lower positioned container.

At step 1640, a determination is made regarding climate variations, wherein high climate (e.g., high altitude, northern geographical location, etc.) may require a lowering of the alcohol content at step 1644, while a lower climate (e.g., lower altitude, more southern geographical location, etc.), may require the alcohol content to be retained the same or raised at step 1642.

Processing then exits with an adjusted alcohol content level.

Although processing 1600 refers to a limited number of factors that may be considered in adjusting a determined alcohol content, it would be within the knowledge of those skilled in the art to include additional factors that may affect the alcohol content of a contained liquid over time. For example, such additional factors may include but not be limited to the condition of the container (the condition of the container may include further elements of the nature of the inner surface (e.g., charred, not charred) of the container), the length of time the container has been in service, the number of times or cycles that the container has been utilized, and the like.

Such additional factors have been contemplated by the inventors and are included within the scope of the invention claimed.

Figure 17:
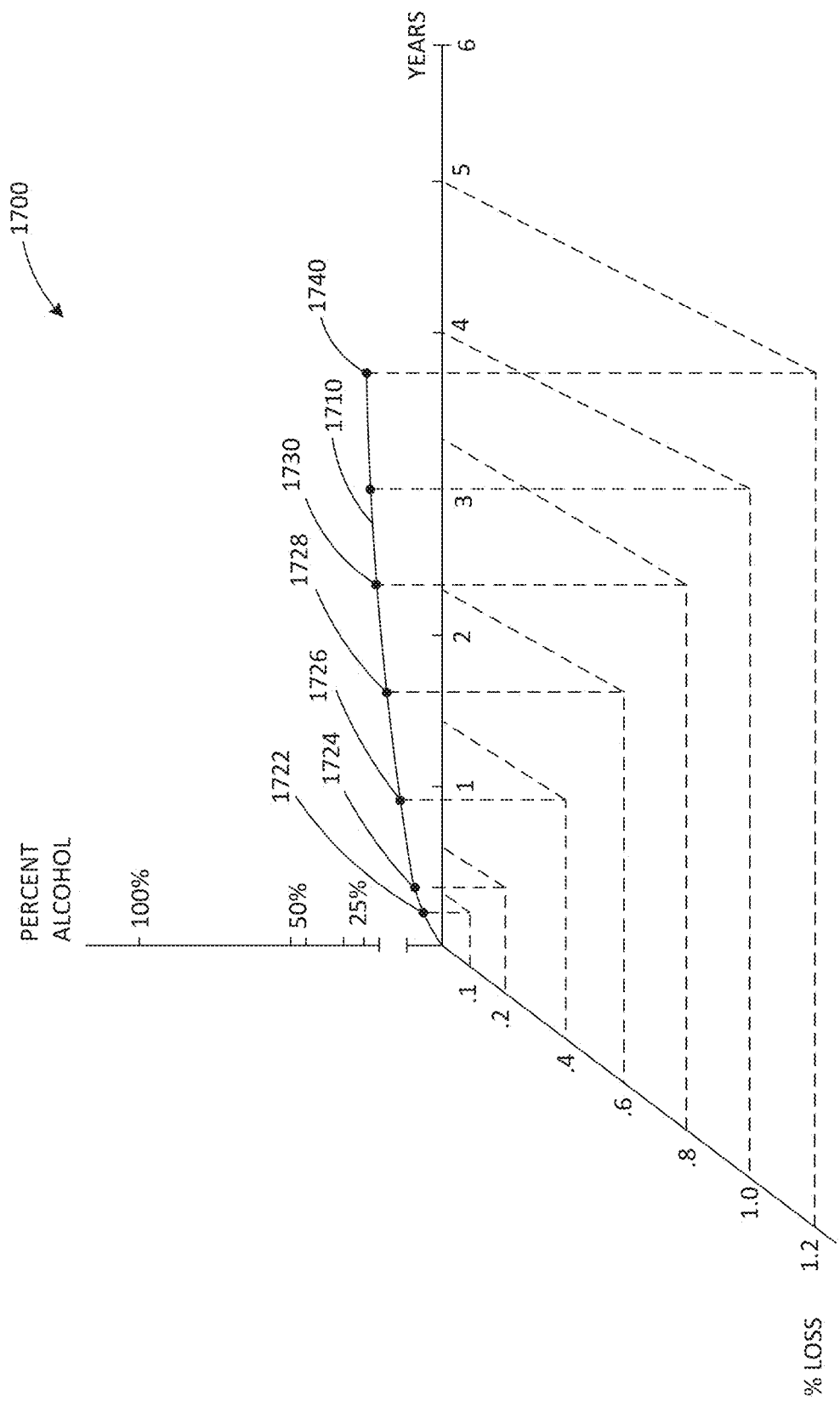
FIG. 17 illustrates an exemplary plotting and extrapolating alcohol content of a liquid within a container in accordance with the principles of the invention.

FIG. 17 illustrates an exemplary plot of determined alcohol content and extrapolating alcohol content in accordance with the principles of the invention.

In this illustrated example, chart 1700 comprises a horizontal axis on to which a number of years of storage of a container is plotted and a vertical axis onto which is plotted a percentage of alcohol content of the contained fluid. In addition, on a third coordinate, is shown that represents a percentage of loss of liquid within the container. Accordingly, a three-dimensional formulation or model of alcohol content versus percentage of fluid loss versus a period of time may be determined, wherein an expected or typical alcohol content may be determined from a determination of a loss of fluid.

Plot line 1710 represents an approximation of a change in alcohol content versus fluid loss, wherein plot line 1710 represents an idealized representation of the development or production of alcohol of the fermenting liquid within the container that may be obtained using mathematical formulation. Alternatively, plot line 1710 may correspond to a series of actual measurements of alcohol content made using conventional methods. For example, measurements or data points 1722, 1724, 1726, 1728, 1730 . . . 1740 may represent one or more measurements of both fluid loss and alcohol content of the fermenting liquid at known periods of time. For example, measurements 1722, 1724 . . . 1740 may be taken periodically (i.e., monthly) or randomly, Based on the measurements or data points 1722-1740, plot line 1710 may then be formulated using statistical methods (e.g., "line of best fit," "least squares," etc.) to produce an approximation of the change in alcohol content that best represents the measured points. Although a "line of best fit" or "least squares" method are discussed, it would be recognized by those skilled in the art that other statistical methods may be utilized to formulate plot line 1710 without altering the scope of the invention claimed.

Figure 18:
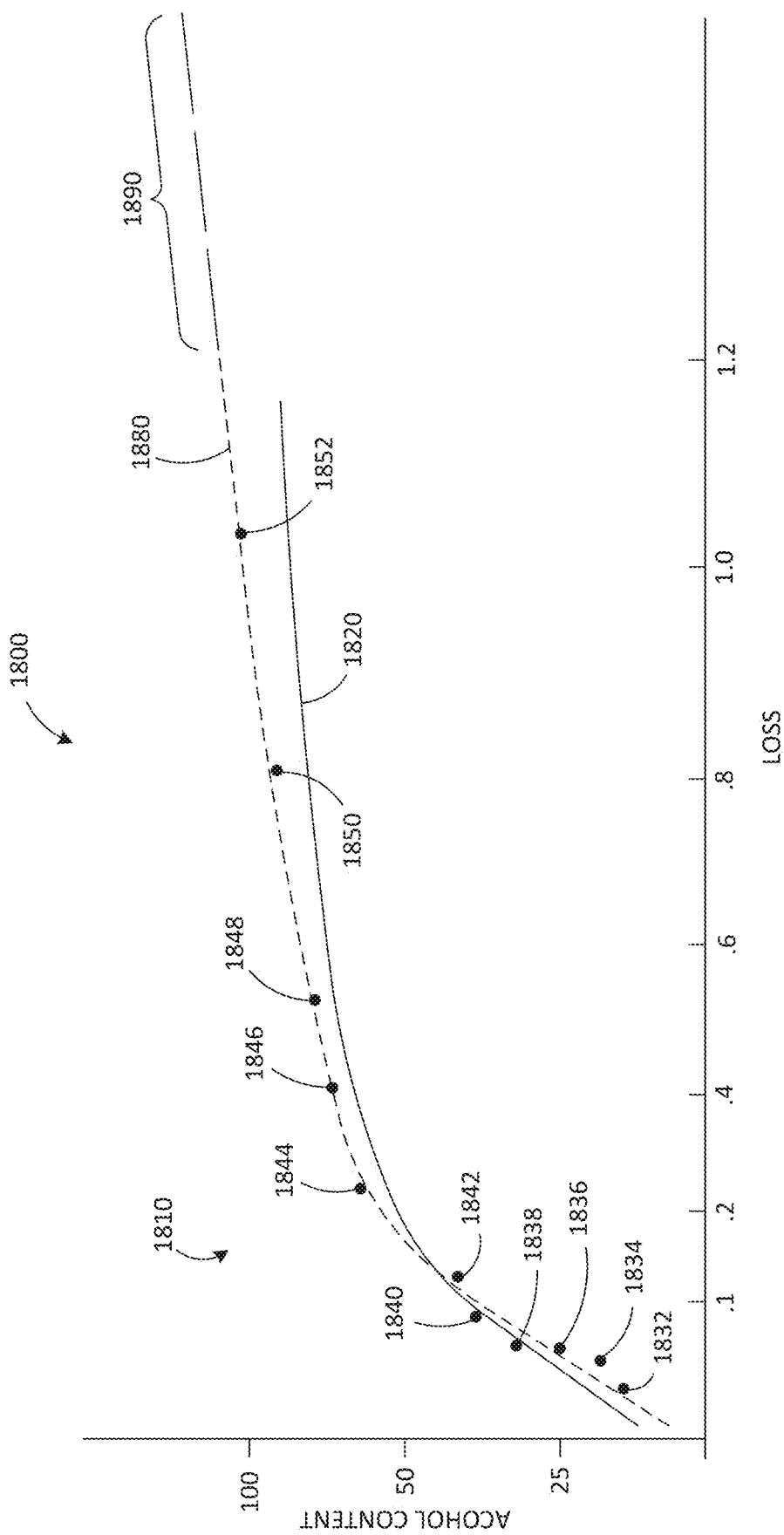
FIG. 18 illustrates an exemplary graph of alcohol content determination in accordance with the principles of the invention.

FIG. 18 illustrates an exemplary graph of alcohol content determination in accordance with the principles of the invention.

FIG. 18 represents a projection 1820 of the idealized or model plot line 1710 onto the two-dimensional plane 1810 of alcohol content verses percent of loss shown in FIG. 17.

In accordance with the principles of the invention, utilizing the idealized projection 1820, an estimate, (i.e., a first order) measure of alcohol content may be determined based on a determined fluid loss. That is, preliminary (i.e., first order) alcohol content measurements may be determined for each of the measurement points based on the determined fluid loss taken at different times. A more refined alcohol measurement may be determined from the preliminary alcohol content at each of the measured (i.e., collected) data points by adjusting or modifying the preliminary alcohol content by one or more environmental factors, as shown and discussed with regard to FIG. 16. Measurements 1832,1834, 1836, 1838 . . . 1852, represent the more refined measurements of alcohol content after considering one or more environmental factors for corresponding ones of the expected alcohol content based on the model shown in FIG. 17.

In accordance with the principles of the invention, the measurements of fluid loss (and determination of alcohol content) may be taken at a first rate during a first period of time while subsequent measurements of fluid loss may be taken at a second rate during a second period of time, wherein the second rate is longer than the first rate. That is, the periodicity of the measurement rate (i.e., first rate and second rate) increases over time.

For example, during a first year, when alcohol production and fluid loss is greatest, fluid loss measurements may be taken at a first rate (e.g., 1832 . . . 1842) and when alcohol production and fluid loss is less, fluid loss measurements may be taken at a second rate (e.g., 1848, 1850, 1852), wherein the first rate is higher (i.e., measurements performed more often) than the second rate.

Further illustrated is a statistical formulation of the measured samples 1832, 1834 . . . 1852, as represented by dashed plot line 1880. Similar to the formulation discussed with regard to FIG. 17, dashed plot line 1880 represents a model that may be provided to refine the model shown in FIG. 17. For example, a plurality of plot lines 1880, taken from a corresponding measurements of a plurality of containers that have similar characteristics (i.e., geographical location) may be accumulated and included in model 1710.

In one aspect of the invention, plot line or model 1880 may be utilized to determine a projection 1890 of an expected alcohol content that when projected onto the plane of alcohol v. years, shown in FIG. 17, may provide information of alcohol production for subsequent years.

Various implementations have been disclosed with reference to the Drawings. However, other implementations are possible. For example, an exemplary method may comprise receiving information regarding an initial state of a liquid in a container, the initial state comprising at least one of: an alcohol measure and a level of the liquid within the container; monitoring a level of the liquid within the container, wherein the monitoring is performed external to the container; determining an amount of loss of the liquid within the container based on the initial level and the monitored level; and estimating the alcohol measure of liquid remaining within the container based on the determined amount of loss of the liquid.

The method may further comprise storing a plurality of estimated alcohol measures.

The method may further comprise extrapolating an expected alcohol measure based on the stored plurality of estimated alcohol measures.

Estimating the alcohol measure may further comprise adjusting the estimated alcohol measure based on at least one environmental condition.

The at least one environmental condition may be selected from a group consisting of: temperature, location within a facility, a geographic location of the facility, and container condition.

The determination of estimating the alcohol measure may be performed periodically.

The rate of periodicity estimating the alcohol measure may be adjustable.

The rate of periodicity estimating the alcohol measure may be increased as a function of time.

An exemplary system may comprise a plurality of antennas positioned on an exterior surface of a barrel, wherein the plurality of antennas are configured to capture signals reflected by a liquid within the barrel; and a processor configured to: receive the reflected signals; and determine a level of the liquid within the barrel, wherein based on the determined level of the liquid within the barrel, the processor is further configured to: determine a loss of liquid within the barrel based on the determined level of fluid and an initial level of fluid; and estimate an alcohol content of the liquid within the barrel based on the determined loss of liquid.

The system may further comprise the processor may be configured to store the estimated alcohol content.

The system may further comprise the processor may be configured to extrapolate an expected alcohol content based on a stored plurality of estimated alcohol measures.

The system may further comprise the processor may be configured to adjust the estimated alcohol content based on at least one environmental condition.

The at least one environmental condition may be selected from a group consisting of: temperature, location within a facility, a geographic location of the facility, and container condition.

The determination of estimating the alcohol content may be performed periodically.

The rate of periodicity estimating the alcohol content may be adjustable.

The rate of periodicity estimating the alcohol content may be adjustable as a function of time.

An exemplary method may comprise: determining, by a monitoring system external to a container, a level of a liquid within the container; and estimating an alcohol content of the liquid within the container based on the determining level of the contained liquid, wherein the estimation comprises: determining an amount of loss of liquid based on the determined level of liquid; obtaining a first order alcohol content based on a model expectation of alcohol content;

and determining the alcohol content based on adjusting the first order alcohol content based on at least one environmental condition.

The at least one environmental condition may comprise at least one of: a temperature, a location within a facility, a geographic location of the facility, and a container condition.

The method may further comprise projecting an estimated alcohol content based on a plurality of the determined alcohol content.

The method may further comprise determining the level of liquid within the container periodically, wherein measurements of the level of liquid is performed at a first rate during a first period of time and at a second rate during a second period of time, the first rate being faster than the second rate.

Figure 19:
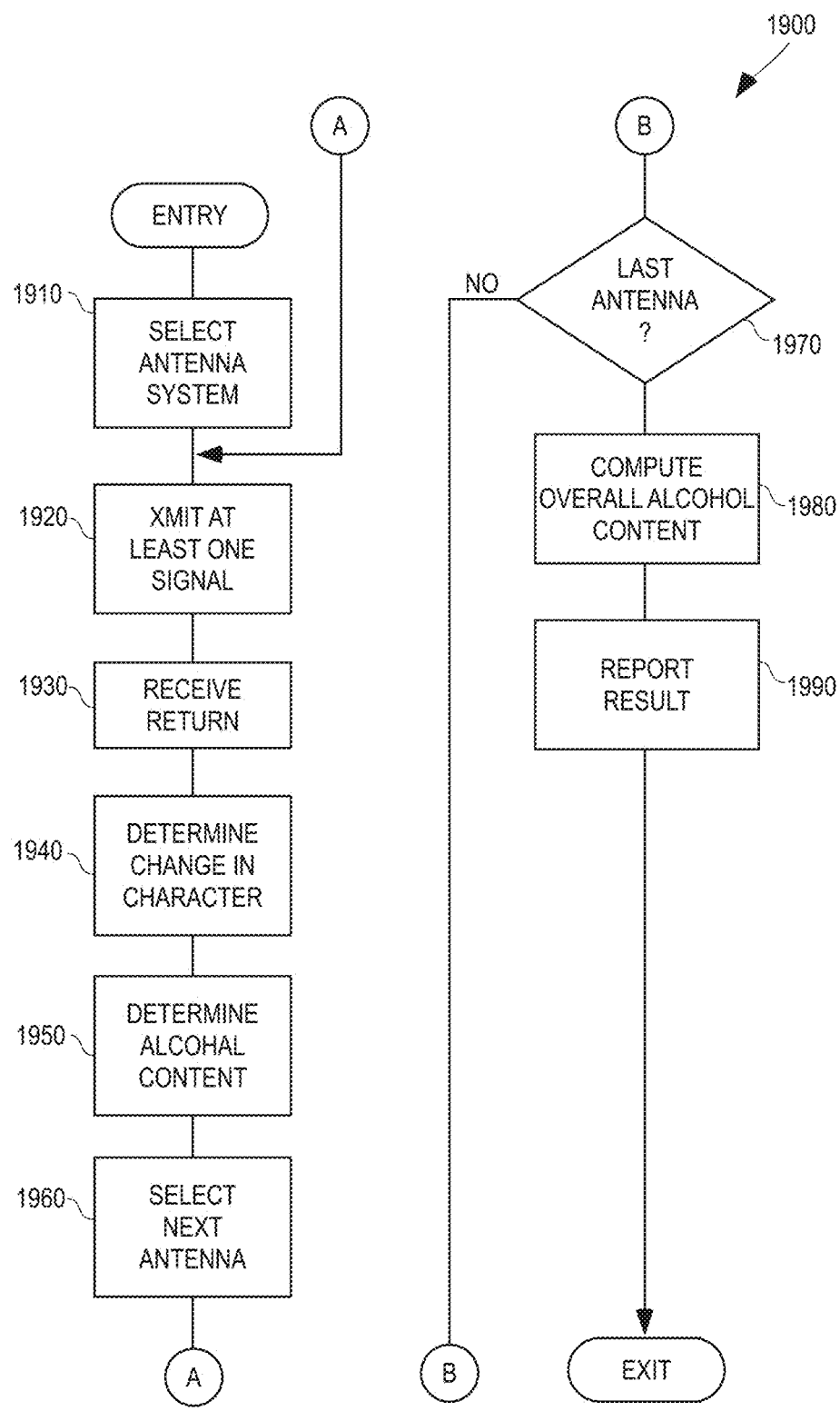
FIG. 19 illustrates a flowchart of a second exemplary process associated with a determination of an alcohol content within a container in accordance with the principles of the invention.

FIG. 19 illustrates a flowchart of a second exemplary process for determining alcohol content of a fluid within a container in accordance with the principles of the invention.

In a further aspect of the invention claimed, the system configurations shown in FIGS. 2, 7A, 7B may be further utilized to determine alcohol content directly. Thus, while alcohol content determination has been discussed with regard to determination of fluid loss, the system may employ a second algorithm in conjunction with or independent of the processing previously disclosed.

In this aspect of the invention, system 150 may implement the illustrated exemplary process 1900, wherein a first antenna from a set of antenna selected from a plurality of antenna associated with the externally mounted antennas shown in FIGS. 2, 7A, 7B is selected at step 1310. In one aspect of the invention, the first antenna among the set of antenna selected may be associated with the lowest position (e.g., 220n) among the illustrated plurality of antenna 220a-220n. Alternatively, the first antenna among the set of antenna may be selected based on a determined level of fluid within the container, wherein the first antenna selected is that antenna that is associated with the highest level of fluid (e.g., the top-most antenna initially). In still a further alternative embodiment, the set of antenna may be selected as a single antenna. For example, the physically lowest positioned antenna may be selected as being included as the sole selected antenna within the set of antenna. In still a further aspect, the sole selected antenna within the set of antenna may be selected as that antenna located physically positioned at or just below the fluid level of the fluid within the barrel. In still a further aspect, the sole selected antenna within the set of antenna may be selected as that antenna physically positioned between the lowest positioned antenna and the antenna positioned at or just below the level of fluid. Although examples of the selection of the one or more antenna selected to be within the set of antenna are disclosed, it would be recognized that other methods of selection of antennas within the set of antenna may be implemented without altering the scope of the invention claimed.

In one aspect of the invention upon filling a barrel or container with a liquid that is to be fermented, a measure of an initial alcohol content may be determined and stored at step 1910. For example, the liquid entered into the container or barrel may represent a mash that has been obtained from a distillation process associated with the fermentation of a base material, such as barley, rye, corn, wheat or a combination thereof.

At step 1920, at least one signal may be transmitted in at least one frequency band from the selected antenna into the contained fluid. A return (i.e., return or reflected signal) associated with each of the transmitted at least one signal is captured at step 1930. At step 1940 a determination of a difference in at least one characteristic (e.g., signal strength, frequency, phase, distance and/or time traveled) between the transmitted signal and the return or reflected signal is made.

In one aspect of the invention, processing system 210 may include a frequency shifting measurement circuit that allows for the determination of a difference between a frequency of the transmitted signal and a frequency of the associated return signal. Alternatively, processing system 210 may include phase shifting measurement circuitry that allows for the determination of a difference between a phase of the transmitted signal and a phase of the associated return signal.

At step 1950, an alcohol content associated with the selected antenna of the fluid within the container may be obtained based on a change in the characteristic (e.g., signal strength, frequency, phase, distance and/or time traveled) of the returned signal.

In one aspect of the invention, the selected antenna may transmit at least one signal (or plurality of signals) at a same frequencies with different phases into the contained fluid, wherein the difference in phase between each of the at least one (plurality of) transmitted signals and the associated returned signal may be determined. In one aspect of the invention, the at least one (plurality of) phase differences may be accumulated and averaged, for example, to obtain an average phase difference. An alcohol content, associated with the selected antenna, may be determined, for example, based on the obtained average phase difference. In another aspect of the invention, the selected antenna may transmit at least one signal (or a plurality of signals) at different frequencies with a same phase into the contained fluid, wherein a difference in frequency between each of the at least one (plurality of) transmitted signal(s) and the associated return may be determined. In one aspect of the invention, the at least one (plurality of) frequency differences may be accumulated and averaged, for example, to obtain an average frequency difference. An alcohol content, associated with the selected antenna may be determined, based on the obtained frequency difference. In still another aspect of the invention, the selected antenna may transmit a plurality of signals at different frequencies and at different phases. Differences in frequency and phase between the transmitted signals and the return signals may be determined, accumulated and averaged to obtain an average frequency and phase values. An alcohol content may be determined based on the averaged frequency and phase values.

At step 1960, a next antenna from the set of antenna of the plurality of antenna is selected. At step 1970 a determination is made whether a last antenna has been selected. In one aspect of the invention, the last antenna may be selected as the last antenna among the plurality of antenna. In another aspect of the invention, the last antenna may be selected as the last antenna associated with a fluid level within the container.

If the last antenna is not selected, processing proceeds to step 1920 wherein at least one signal is transmitted by the selected antenna and the processing illustrated by at least steps 1930 to 1950 for obtaining alcohol content associated with the selected antenna is performed.

However, if the last antenna of the set of antenna has been selected, then processing proceeds to step 1980, wherein an average (or a median) alcohol content may be determined based on the previously determined alcohol content associated with each of the selected antenna. At step 1990, a report of the determined alcohol content may be provided.

In one aspect of the invention, the average (or median) alcohol content may be determined based on a filtering of the alcohol content associated with each of the selected antenna. For example, the average (or median) alcohol content may be obtained by removing a high alcohol content and a low alcohol content from the collected set of alcohol content in order to remove singular values. Alternatively, the average (or median) alcohol content may be obtained by first removing the alcohol content associated with the last selected antenna and averaging or accumulating the remaining values. In this manner, the determined average (or median) alcohol content obtained is not influenced by an alcohol content at the fluid/air boundary.

Although, the process shown in FIG. 19 contemplates determining an alcohol content from the determined alcohol content associated with each of the selected antenna, it would be recognized by those skilled in the art that resultant characteristics (e.g., signal strength change, frequency shift, phase shift, change in distance and/or time traveled, etc.) may be obtained for each of the selected antenna, and an alcohol content may be obtained based on a resultant characteristic obtained over all the selected antenna within the set of antenna.

In accordance with the principles of the invention, the alcohol content obtained utilizing the processing shown in FIG. 19 may be further adjusted in a manner similar to that described with regard to FIGS. 15 and 16.

In still another aspect of the invention, the alcohol content obtained utilizing the processing shown in FIG. 19, may be correlated with the alcohol content obtained utilizing the processing shown in FIG. 14. Alternatively, the alcohol content obtained utilizing the processing shown in FIG. 19, may supplement the alcohol content obtained utilizing the processing shown in FIG. 14 to improve the model as shown in FIGS. 17 and 18.

FIGS. 20A-D illustrate exemplary charts of alcohol content of a liquid within a container for different transmitted frequencies.

Figure 20A:
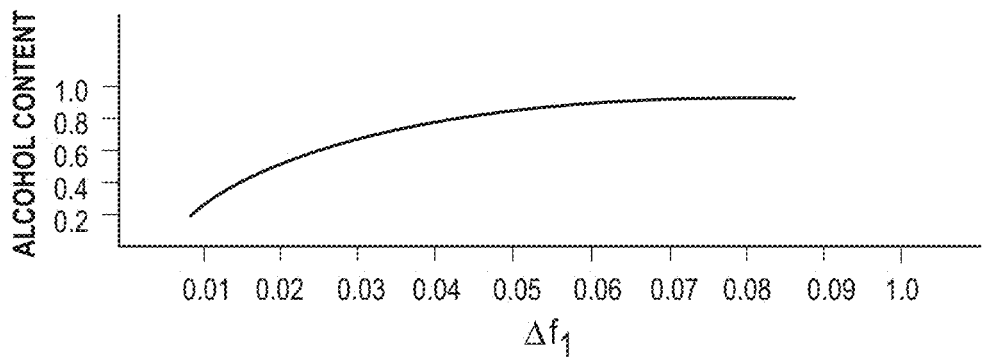
FIGS. 20A-D illustrate exemplary charts of alcohol content as a function of change in frequency.

FIG. 20A illustrates an exemplary chart (or mapping) of an alcohol content of a liquid within a container over a transmitted frequency wherein the transmitted signal frequency is represented as $f_1$. In this exemplary chart alcohol content is represented on a vertical axis and a frequency difference ($\Delta f_1$) between a transmitted signal and a return signal is shown on a horizontal axis. As shown, as the alcohol content increases, the expected difference in frequency between the transmitted signal and the return signal increases. Accordingly, a measurement of the frequency difference provides a means for determining an alcohol content of a fluid or liquid within the container.

Accordingly, a measurement of the frequency difference provides a means for determining an alcohol content of a fluid or liquid within the container.

Figure 20B:
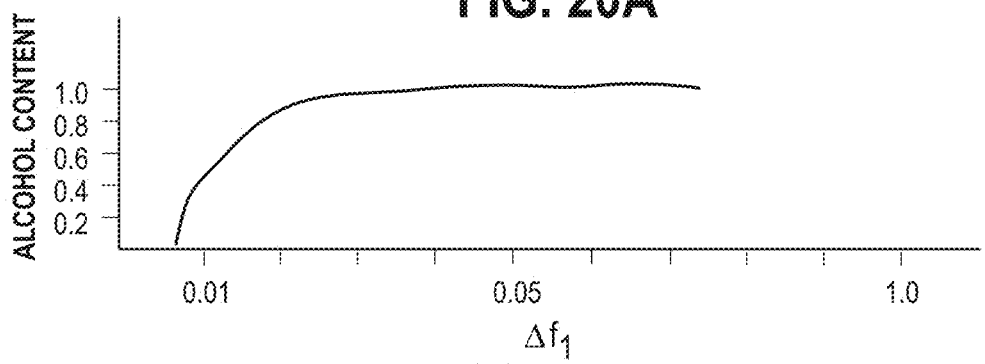
Figure 20C:
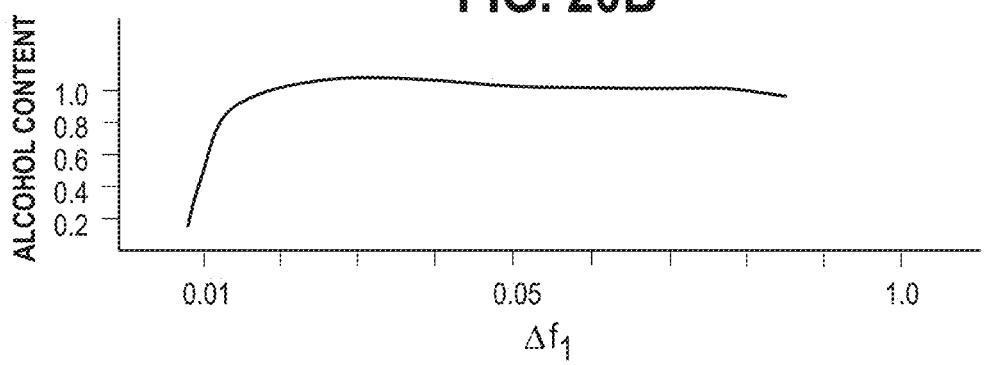
Figure 20D:
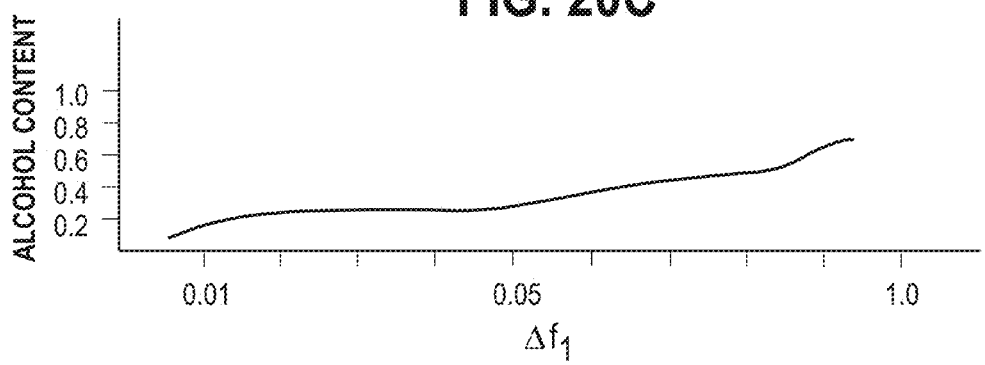

FIGS. 20B-20D represent charts, similar to the chart shown in FIG. 20A, representing a measure of alcohol content associated with a fluid or liquid for different transmitted frequencies (represented as $f_2$, $f_3$, $f_4$ respectively).

Accordingly, an alcohol content may be determined for each of a plurality of measured frequency returns for each of the selected antenna configurations. Accordingly, an overall alcohol content may be determined based on the collection of one or more alcohol content taken over one or more frequency measurements over one or more antenna configurations.

Although only four (4) frequencies are illustrated, it would be within the knowledge of those skilled in the art to create additional charts showing frequency shift as a function of alcohol content without undue experimentation. As the number of charts similar to those shown in FIGS. 20A-20D is expanded, the accuracy of the measurement of alcohol content would increase as the number in the transmitted frequencies increases.

Although FIGS. 20A-20D illustrate exemplary charts of alcohol content as a function of change in frequency, it would be recognized by those skilled in the art that a similar set of exemplary charts may be obtained as a function of phase change, signal strength change, change in distance and/or time traveled or other similar characteristic associated with the transmitted signal, without altering the scope of the invention claimed.

Figure 21:
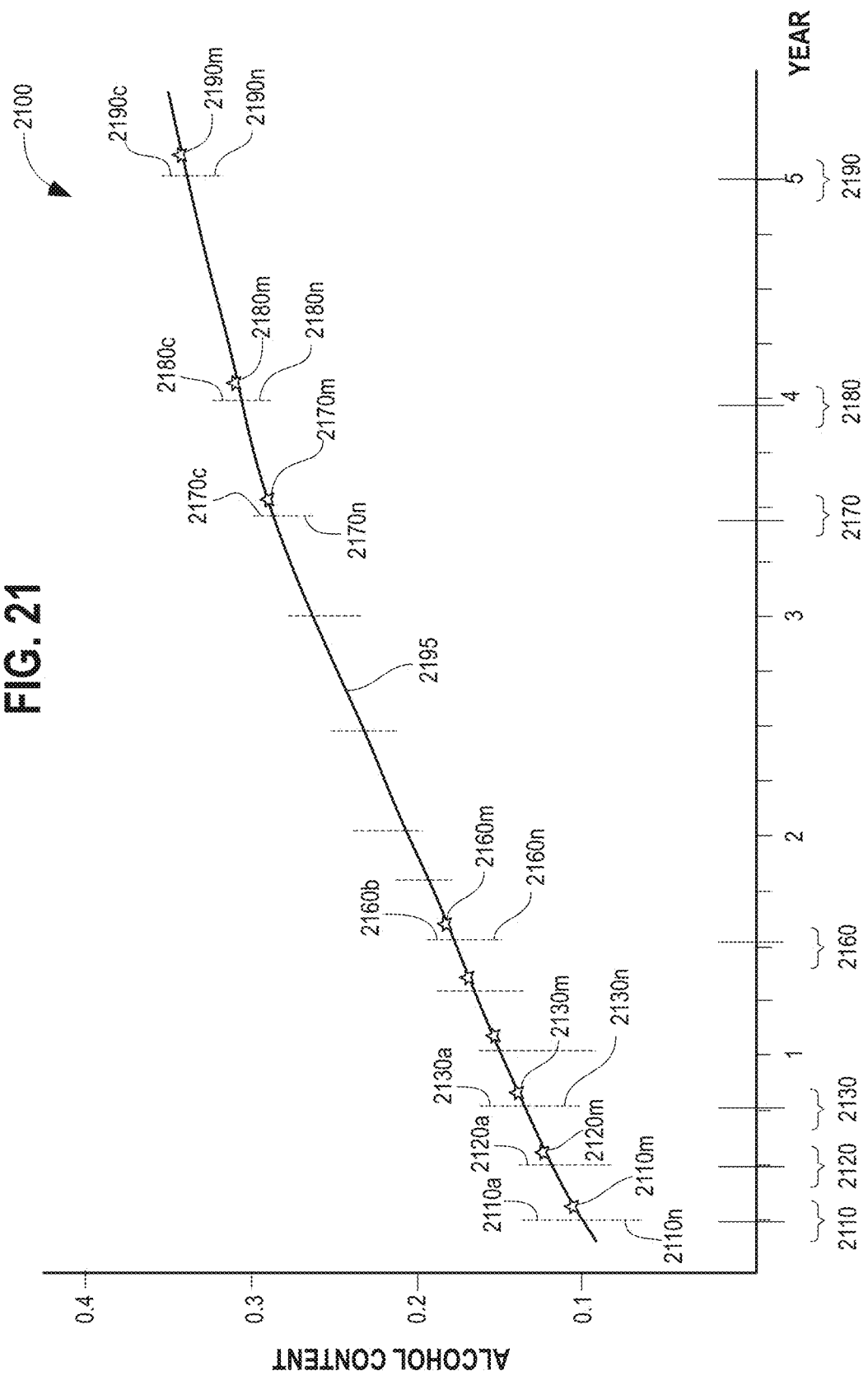
FIG. 21 illustrates an exemplary chart of measurement of alcohol content as a function of time.

FIG. 21 illustrates an exemplary chart of determined alcohol content as a function of time in accordance with the principles of the invention.

In this illustrated example, chart 1500 represents a plurality of measurement sets 2110, 2120, 2130, 2140, 2150, 2160, 2170, 2180 and 2190 that are taken at intervals over a period of time. For example, the measurements 2110a-2110n associated with measurement set 2110 represent a measured alcohol content for each of a plurality of antenna 220a-220n (similar to the configurations shown in FIGS. 2, 7A and 7B). In this illustrated example, the value of "n" is selected as eight (8) to illustrate the principles of the invention. Similarly, the measured data points are shown as individual data points linearly spaced apart to show the individual measurements. Generally, it would be expected that one or more measurements or measurement points a-n of any measurement set 2110, 2120, 2130, 2140, 2150, 2160, 2170, 2180 and 2190 may be the same or substantially the same.

In addition, each of the illustrated measurement points 2110a-2110n may represent an accumulated value taken over multiple transmission frequencies (and/or phase) measurements (e.g., frequencies $f_1$, $f_2$, $f_3$, $f_4$, as shown in FIGS. 14A-14D). For example, measurement set 2120 and 2130 represent similar measurements taken, in this illustrated case, at a first known rate (e.g., quarterly) during a first or initial period (i.e., first year).

In accordance with the principles of the invention, an average or median value (i.e., 2110m) associated with measurement points 2110a-2110n of measurement set 2110 may be calculated to determine an alcohol content associated with measurement set 2110. Similarly, median values 2120m, 2130m associated with measurements 2120a-2120n, 2130a-2130n, respectively, may be calculated to represent an overall alcohol content for measurement sets 2120, 2130, respectively. Similar average or median values may be determined for each of the measurement sets 2140-2190.

Accordingly, a median alcohol content for each of the illustrated measurement sets 2110-2190 may be determined and utilized to determine a progression of alcohol content of the liquid or fluid within a container without the need to interrupt the process by taking conventional measurements.

Further illustrated, with regard to measurement set 2160 are measurements 2160b-2160n associated with antenna 220b-220n. In this illustrated example, as evaporation or absorption of the fluid within the container occurs, it may be determined that a signal transmitted by antenna 220a provides no useful information and, thus, a signal from antenna 220a is not transmitted nor included within the calculations of an overall alcohol content (i.e., 2160m). A similar selection of antenna is shown by measurement sets 2170-2190 where signals associated with antenna 220b are neither transmitted nor included within the calculation of overall alcohol content (e.g., 2170m-2190m).

In accordance with the principles of the invention, the measurements of fluid loss (and determination of alcohol content) may be taken concurrently at a first rate (e.g., quarterly) during a first period of time (e.g., first and second year) while subsequent measurements of fluid loss and alcohol content may be taken concurrently at a second rate (semi-annually, annually) during a second (e.g., $2^{nd}$ and $3^{rd}$ year, $4^{th}$ and $5^{th}$ year) period of time, wherein the second rate is longer than the first rate. That is, the periodicity of the measurement rate (i.e., first rate and second rate) may increase over time.

For example, during a first year, when alcohol production is greatest, measurements may be taken at a first rate (e.g., measurement sets 2110, 2120 . . . 2160) and when alcohol production is less, measurements may be taken at a second rate (e.g., 2170, 2180, 2190), wherein the first rate is higher (i.e., measurements performed more often) than the second rate.

Alternatively, the measurement of fluid loss and alcohol content progression may be taken asynchronously wherein fluid loss may be determined at a fluid loss first and second rate as previously discussed and alcohol content progression may be determined at an alcohol progression first and second rate, wherein the fluid loss rates and the alcohol progression rates are different.

Further illustrated is a statistical formulation of the measured sets 2110m-2190m as represented by dashed plot line 2195. Dashed plot line 2195 represents a model that may be utilized to refine the models shown in FIG. 20A-20D. For example, a plurality of plot lines 2195, taken from a corresponding measurements of a plurality of containers that have similar characteristics may be accumulated and included in the model shown in FIGS. 20A-20D.

FIG. 21, similar to FIG. 18, illustrates the variation in the time period between measurements that may occur for the measurement of an alcohol content associated with the processing shown in FIG. 19. As previously discussed, the time period of measurement for alcohol content may occur concurrently with the time period of measurement for fluid level shown in FIG. 18. However, it would be recognized that the time period for alcohol content determination may be different than the time period of measurement for fluid level. Thus, the two processes shown may operate concurrently or independently without altering the scope of the invention claimed.

In accordance with one aspect of the invention, the transmitted signal discussed may comprise a Frequency Modulated (FM) signal, in which the frequency of the transmitted signal is varied (i.e., modulated) during the duration of the transmitted signal. In this manner, the fluid loss, as discussed, may more accurately be determined, as the alteration or change of the transmitted frequency during a specific period provides for different time of returns of the transmitted frequency. Thus, the signals during each of the transmissions 570, 580, 590, etc., shown in FIG. 5B, may comprise a plurality of frequencies (i.e., frequency modulate), wherein the corresponding return windows may be varied based on the transmitted frequency. For example, the transmission signal within a transmission may be continuously varied from a first frequency to a second frequency Alternatively, the transmission signal with a transmission may be discretely altered in a known pattern (e.g., f1, f1+x, f1+2x, etc.) in still another aspect the frequencies within a transmission may be varied (i.e., modulated) in a pseudo-random pattern (e.g., f1, f1+x, f1−2x, f1−x, . . . , etc.). In this manner the time of the return signals associated with each of the transmitted signals may be varied (i.e., modulated) based on the transmitted frequency. In one aspect of the invention, the transmitted signals may be transmitted as Frequency Modulated Continuous Wave (FMCW) signals. In another aspect of the invention, the transmitted signals may be transmitted as pulse signals within a frequency of each of the pulses within a transmission is modulated. In still another aspect, each of the pulses within a transmission may comprise a "chirp" signal, wherein the frequency of a transmitted signal is varied during the transmission of a pulse signal.

In one aspect of the invention, the range of frequency variation may vary based on a determined distance, as will be discussed. In another aspect of the invention, the starting frequency value for each of the signal transmissions 1105, 1115 (FIG. 11A) or the transmissions 570, 580 . . . within each of the transmissions 1105, 1115 . . . (FIG. 11B) may be varied. Alternatively, the pattern of frequency modulation with signal transmissions 1105, 1115 . . . or transmissions 570, 580 . . . with transmission 1105, 1115 . . . may be varied.

Although FIGS. 11A and 11B illustrate time variable transmissions, it would be recognized that the interval being transmissions may be increased, decreased or remain steady over time.

In one aspect of the invention, an average value of the time of the return signals may be determined to determine an overall time that may be used to determine at least one of a fluid level, a mash level and a solid material level. Alternatively, a filtering of the return times may be made to remove those times that are not representative of returns. For example, the highest return time and the lowest return time may be removed from any calculation of an overall time based on the remaining return times.

In accordance with the principles of the invention, a measure of different content of a container may be determined based on different returns of the modulated signal transmission. For example, in a content comprising both a fluid, a mash (i.e., fluid plus solid content) and a solid content, the signals returns associated with the different content may vary based on the transmitted frequency. For example, selected frequency transmissions may result in returns that are reflected from the fluid, selected other frequency transmission may result in returns that are reflected from the mash and selected other frequency transmissions may result in returns that are reflected from the content.

Figure 22:
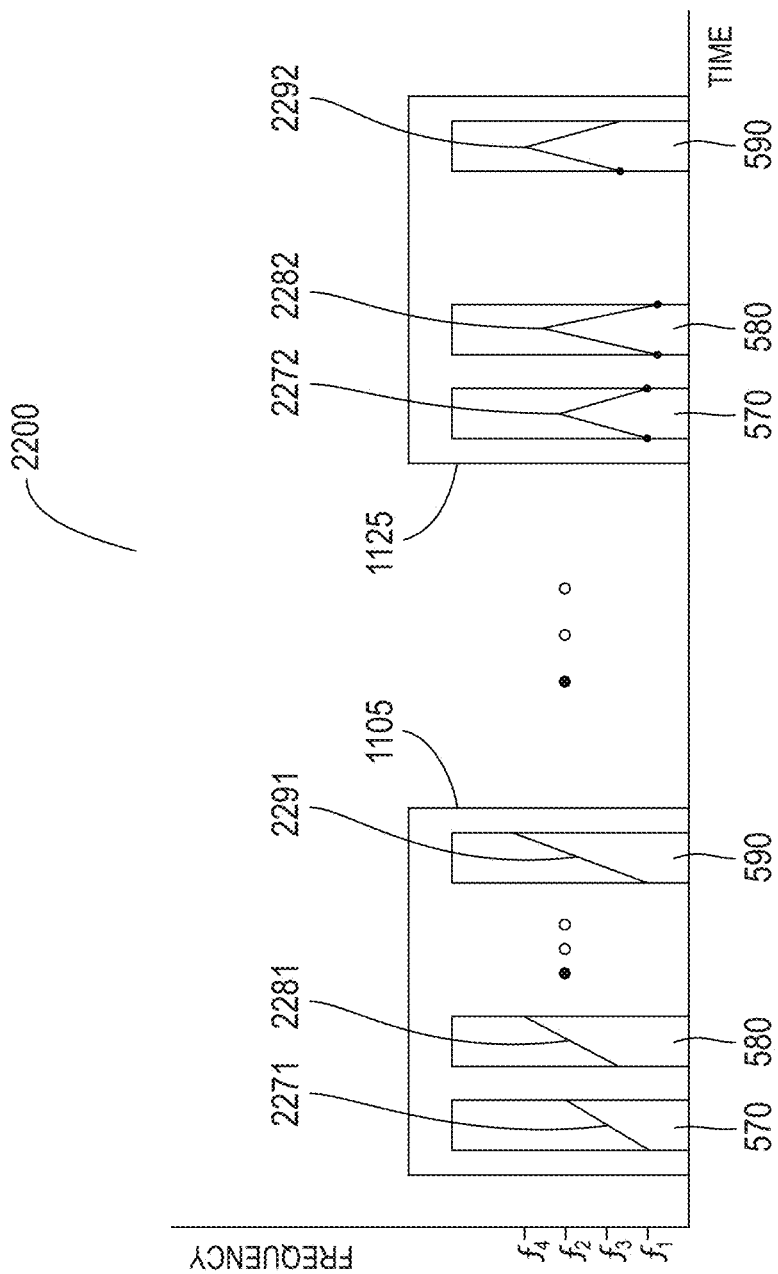
FIG. 22 illustrates an exemplary example of a transmission sequence in accordance with the principles of the invention.

FIG. 22 illustrates an exemplary example of a transmission sequence in accordance with the principles of the invention.

In the illustrated exemplary transmission sequence 2200, which is similar to the sequence shown in FIGS. 11A-11C, transmissions are shown as a function of time (X-axis) and frequency (Y-axis). As shown in FIG. 22, transmissions 570, 580 . . . 590 within a single burst transmission 1105 may comprise one or more transmission frequency changes, wherein the transmission frequency is varied. For example, during transmission 570 during interval 1105 the signals emitted vary between frequency f1 and f2. Similarly, during transmission 580 of interval 105, the signals transmitted or emitted vary between f3 and f4. Similar frequency variation occur for transmission 590. In the illustrated examples, the frequencies are transmitted, within a single transmission, in a continuous pattern (e.g., sawtooth).

In another example, shown with regard to burst transmission 1125, the frequencies within a single transmission 570, 580, . . . 590 may be modulated, which in this case is shown as sinusoidally or triangularly modulated (e.g., upward and downward).

Further illustrated is the starting and stopping frequencies within each of the single transmission 570, 580, . . . 590 within a corresponding burst transmission 1105, 1125 may be different in the selection of the different starting frequencies (e.g., f1, f3, etc.), the rate of frequency modulation and the type of frequency modulation (e.g., sawtooth, triangular, pseudo-random etc.) may be determined, in part, based on the type of material (i.e., fluid, mash, solid) that is being evaluated. For example, for a container containing only fluid (e.g., water tower), a single same starting frequency may be selected wherein the modulation may be one of unmodulated or modulated using a sawtooth pattern. In another example, wherein both fluid and mash are expected with a container, a plurality of frequencies may be selected, wherein the starting frequency and modulation type may be varied to provide diversity to the timing of the return frequencies may be evaluated to obtain a picture of the container (i.e., level of mash and level of fluid atop the mash).

As discussed with regard to FIG. 5B, a return window may be established for each of the transmitted frequencies, wherein the timing of the return window may increase, or decrease based on the transmitted frequency and the expected content.

As would be appreciated by those skilled in the art, the return window may be initially set as a large number (to accommodate an empty tank) and decreased as the tank fills with one or more of a fluid, a mash or a solid content, as the level of the contained content (e.g., solid content) would not decrease (only increase) over time. Hence, the expected return window time may be decreased as the return signal is expected is a shorter time.

In one aspect of the invention, the system shown in FIGS. 7A and 7B may comprise a single transmission antenna to transmit a plurality of signals at different frequencies and frequency ranges (or a plurality of antennae if different frequency ranges require different antenna capabilities) and a receiving antenna to receive a plurality of signals at different frequencies and frequency ranges (or a plurality of antennae if different frequency ranges require different antenna capabilities). The receiving antenna and the transmitting antenna may be separated wherein the transmitting antenna transmits a signal into the container at an angle wherein the reflection is returned to the receiving antenna at substantially the same angle. The angle of transmission may further be altered as the level of the content within the container increases. As the steepness of the angle of transmission decreases (i.e., from an axis perpendicular to the monitoring system), a limit factor may be established such that an alarm is generated when the steepness of the transmission angle falls below a threshold. Thus, as the angle of transmission decreases from 70 degrees to 20 degrees with regard to an axis perpendicular to the monitoring system, an alarm may be trigged to indicate the level of fill of one or more of the content within the container.

Figure 23:
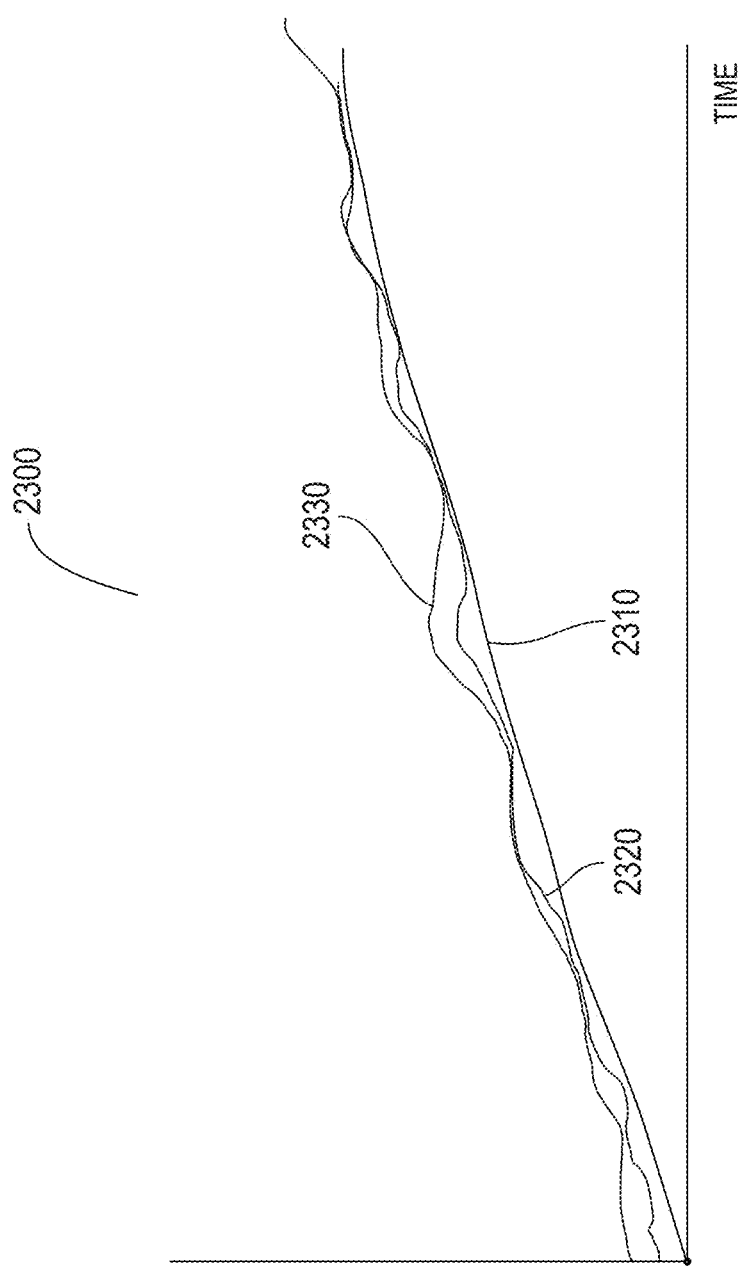
FIG. 23 illustrates an exemplary chart of the collection of one or more materials within a container monitored by the external monitoring system disclosed herein.

FIG. 23 illustrates an exemplary chart of the collection of one or more materials within a container monitored by the external monitoring system disclosed herein.

In this exemplary chart 2300, solid content 2310 accumulates over time from a zero value to a greater value. The solid material generally increases over time as there is no means for removing the material during the monitoring period. The amount of a mash material, i.e., a mixture of fluid and solid material 2320 similarly over time. However, the amount of mash material increases randomly over time as the fluid within the mash is dispensed, while the remainder of the mash material becomes of a more solid content as the mash settles on-top of the solid material and the fluid is removed. The amount of fluid material, 2330 similarly, increases over time. However, because means for removing the fluid material from the container may exist, the amount of fluid also decreases over time such that the fluid first mixes with the mash material and is later dispensed.

In one aspect of the invention, the frequencies of transmission shown in FIG. 22, may be based, in part, on the content of the container. For example, in a new configuration transmission signals may comprise a single frequency or range of frequencies as the expected content is limited to fluid, whereas the number of frequencies and/or ranges (and the variations of frequencies and ranges) may increase as different types of content are detected within the container. Thus, as solid content increases, a frequency and/or frequency range applicable to solid content may be introduced into the transmission sequence. Returning to FIG. 22, transmissions 570, 580 . . . 590 within burst transmission 1105 may include only a single frequency (or frequency range) transmission whereas the transmissions 570, 580, 590 within burst transmission 1125 may include a plurality of frequency (and/or frequency ranges). The starting frequencies of the plurality of transmitted signals may be selected to be the same or different.

Although FIG. 22 illustrates a plurality of transmitted signals 570, 580, . . . 590, if would be recognized that in aspects of the invention, wherein only a signal transmitting antenna is utilized (see FIG. 1, for example), then only a signal transmitting may occur during each interval. Alternatively, a plurality of transmitted signals may occur during each interval wherein the transmitted signal is the same. The number of transmitted signals and the frequency of each interval may be adjusted to conserve power (in a battery-operated configuration).

The level of solid content and/or the fill rate may be monitored such that a condition of the tank or container may be determined and potential issues regarding overflow, for example, may be averted. In one aspect of the invention, the information collected from the level of the content within the tank or container may, as previously discussed, be provided to one or more external or remote sites such that the information is provided to appropriate personnel.

Hence, in the application of the external monitoring systems disclosed in FIGS. 7A and 7B, which has been discussed with regard to fluid measurement and alcohol content within a barrel or container, it would be recognized that the configuration shown in FIG. 1, for example, would be application to other systems that are arranged in this manner.

For example, a conventional septic system, wherein in a measurement of a solid content within the septic system may be determined. In another application of waste management, wherein large amounts of waste product are contained in containers (or pools), a measurement of the solid content within the container may be used to determine when appropriate dredging operations are to occur. In addition, the external monitoring system disclosed may further provide information regarding a rate of fill or collection of solid materials. In addition, the information collected by the external monitoring system disclosed may provide an indication that the health of a collection system, when the collection system is performing not performing properly. For example, a determined level of fill of solid content may trigger a message that the system is near capacity and cleaning and/or removal of the solid material is needed.

In another aspect, the maintenance of fluid within the system may be an indication of the improper egress of the fluid from the system.

In one aspect of the invention, and as previously discussed, information regarding the level of solid content, the level of fluid level and/or the health of the system may be transmitted to one or more external devices to provide information to those persons needing such information to manage the system (e.g., homeowner, site managers, etc.).

In one aspect of the invention, and as discussed previously, the measurement of content (i.e., fluid and/or solid material) can be recorded and provided to external (or remote) monitoring systems over time such that a projection of fill rate may be determined. The projection, which may be adjusted and/or modified, over time provides a means for determining potential failures. In addition, the collected recorded data may be used to provide information regarding regulatory compliance with required environmental monitoring. The providing of the determined data may be transferred to one or more external systems through one or more of: a wired connection and a wireless connection (e.g., Wi-Fi, BLUETOOTH, etc.). In still another aspect, the collected data may be retained locally and downloaded onto tangible medium (e.g., USB drive) for subsequent processing by one or more external or remote devices.

Although the example provided with regard to employing the external monitoring system for the monitoring of content (e.g., fluid, mash, solid waste) of a septic system, it would be understood that the system disclosed would be applicable to other systems. For example, in a commercial wastewater management systems (or underground storm drains, retention pond water levels, etc.) measurements made using the disclosed system may provide information to be used in determining with required regulatory compliance standards and sustainability. The external monitoring system disclosed would also be applicable to fluid storage systems (e.g., storing oil, fuel, chemical and water tanks). Or to agricultural systems such as irrigation reservoirs, manure pits or livestock waste.

In accordance with the principles of the invention, the non-invasive monitoring system provides a modern, reliable and low maintenance solution for tracking fluid/waste content, which replaces outdated invasive methods or devices (e.g., float sensors, manual inspection). The non-invasive system provides a more reliable, lower cost solution to the content management that ensures detection of early problems, reduced maintenance costs and improved environmental compliance.

Although the monitoring systems disclosed, herein, have made reference to the use of radio frequency transmission, it would be recognized by those skilled in the art that the signals transmitted may be in the ultra-sonic range. Transmission of ultra-sonic signals may be suitable for systems that are an area in which radio frequency transmission is not suitable or allowed. Signals transmitted in an ultra-sonic frequency range may be transmitted as discussed using steady transmission or frequency modulated transmissions.

Various implementations have been disclosed with reference to the Drawings. However, other implementations are possible.

Implementation 1. A method for determining an alcohol content of a fluid within a barrel, the method comprising the steps of: transmitting at least one signal from each antenna within a set of antenna selected from among a plurality of antenna positioned externally to the barrel into the barrel; receiving a response associated with the transmitted at least one signal, determining a change in at least one characteristic between corresponding transmitted at least one signal and the received response; determine a change of a characteristic between the at least one transmitted signal and a corresponding received response; and determine from the determined change in the characteristic an alcohol content of the fluid within the barrel based on a mapping of an alcohol content with respect to the change in characteristic.

Implementation 2. The method of implementation 1, wherein the step of determining a change in characteristic comprises the steps of: accumulating the change in characteristic between each of the at least one transmitted signal and the corresponding received response; and setting the determined change in characteristic as the accumulated change in characteristics.

Implementation 3. The method of implementation 2, wherein the step of determining a change in characteristic comprises the steps of: averaging the accumulated change in characteristic between each of the at least one transmitted signal and the corresponding received response; and setting the determined change in characteristic as the average accumulated change in characteristic.

Implementation 4. The method of implementation 1, wherein the characteristics is selected from at least one of: a signal strength, a frequency shift, and a phase shift.

Implementation 5. The method of implementation 1, wherein the step of determining a change in characteristic comprises the steps of: determining an average value of the change in characteristic for each of the at least one signal for each of the antenna within the set of antenna; determining an alcohol content for each of the average values; and determining an overall alcohol content based on the determined alcohol content for each of the average values.

Implementation 6. The method of implementation 1, comprising: identifying among the plurality of antenna, an antenna positioned within a range of the fluid within the barrel; and selecting the identified antenna as being within the set of antenna.

Implementation 7. The method of implementation 6, wherein the step of identifying comprises the steps of: transmitting from the plurality of antenna, a measurement signal into the barrel; receiving a return signal of the transmitted measurement signal; determining a signal strength of the received return signal, and identifying an antenna associated with a signal strength greater than a threshold value as being within the range of the fluid.

Implementation 8. The method of implementation 1, transmitting at least one signal from each antenna comprises the steps of: transmitting at a first rate during a first period of time; and transmitting at a second rate during a second period of time.

Implementation 9. The method of implementation 8, wherein the first rate is greater than the second rate.

Implementation 10. A system for determination of an alcohol content of a fluid within a barrel, the system comprising: a plurality of antenna positioned external to the barrel; and a transmission/reception system configured to: transmit at least one transmission signal within at least one frequency band from a set of antenna selected from the plurality of antenna; receive a return signal associated with the transmitted at least one transmission signal; and determine a change in at least one characteristic between the at least one transmission signal and a corresponding return signal; and determine from the determined change in the at least one characteristic an alcohol content of the fluid based on a mapping of alcohol content with respect to the change in the at least one characteristic.

Implementation 11. The system of implementation 10, wherein the change in the at least one characteristic comprises at least one of: a signal strength change, a frequency change or a phase change.

Implementation 12. The system of implementation 10, wherein the transmission/reception system is configured to:

determine the change in the at least one characteristic as an average of the change in the at least one characteristic over each determined change in the at least one characteristic.

Implementation 13. The system of implementation 10, wherein the transmission/reception system is configured to: determine an average change in the at least one characteristic as: an average value of the change in the at least one characteristic over each of the at least one determined change in the at least one characteristic for corresponding ones of the antenna within the set of antenna; and an average of the average values.

Implementation 14. The system of implementation 10, wherein set of antenna comprises at least one antenna associated with a determined level of fluid within the barrel.

Implementation 15. The system of implementation 14, wherein the system is configured to: transmit a measurement signal into the barrel from an antenna selected from the plurality of antenna; receive a return signal associated with the measurement signal; determine a signal strength of the return signal; and assign, when the signal strength is greater than a threshold value, a corresponding antenna selected from the set of antenna.

Implementation 16. A system for determining an alcohol content of a fluid within a barrel, the system comprising: a plurality of antenna arranged at known locations on a face of the barrel; and a processing system comprising: a transmitting system and a receiving system in communication with each of the plurality of antenna; and a processing system configured to: receive, from the receiving system, information regarding a signal transmitted into the barrel by the transmitting system, wherein the information is associated with the signal transmitted to determine a level of fluid within the barrel and an alcohol content of the fluid within the barrel, wherein a determination of the level of fluid comprises: causing transmission of a measurement signal from each of the plurality of antenna; receiving a response associated with the transmitted measurement signal; and determining at least one factor associated with the received response; and assigning, when the at least one factor is greater than a threshold value, a corresponding antenna to a set of antenna; and wherein the determination of the alcohol content comprises: causing the transmission of at least one signal from each of the antenna within the set of antenna; receiving at least one return signal in response to the transmission of the at least one signal transmission; determining a change in a characteristic between the at least one signal transmission and a corresponding return signal; and determining an alcohol content associated with the fluid within the barrel as a function of a mapping of alcohol content with respect to the change in the characteristic.

Implementation 17. The system of implementation 16, wherein the processing system is further configured to periodically perform the determination of fluid level and alcohol content, and wherein a rate of performance of the determination of fluid level and alcohol content may be the same or different.

Implementation 18. The system of implementation 16, wherein the mapping of alcohol content with respect to change in characteristic is established on an individual transmission frequency basis.

Implementation 19. The system of implementation 16, wherein performance of the determination of alcohol content is performed starting with a lowest positioned antenna within the set of antenna.

Implementation 20. The system of implementation 16, wherein performance of the determination of alcohol content is performed starting with a highest positioned antenna within the set of antenna.

For example, an exemplary method may comprise receiving information regarding an initial state of a liquid in a container, the initial state comprising at least one of: an alcohol measure and a level of the liquid within the container; monitoring a level of the liquid within the container, wherein the monitoring is performed external to the container; determining an alcohol content of the liquid within the container based on the initial level; and estimating the alcohol measure of liquid remaining within the container. In addition, a measure of the loss of fluid in the container may be used to limit the measurements taken to only those configurations that would provide useful information in determining the alcohol content.

The method may further comprise storing a plurality of estimated alcohol measures.

The method may further comprise extrapolating an expected alcohol measure based on the stored plurality of estimated alcohol measures.

Estimating the alcohol measure may further comprise adjusting the estimated alcohol measure based on at least one environmental condition.

The at least one environmental condition may be selected from a group consisting of: temperature, location within a facility, a geographic location of the facility, and container condition.

The determination of estimating the alcohol measure may be performed periodically.

The rate of periodicity estimating the alcohol measure may be adjustable.

The rate of periodicity estimating the alcohol measure may be increased as a function of time.

An exemplary system may comprise a plurality of antennas positioned on an exterior surface of a barrel, wherein the plurality of antennas are configured to capture signals reflected by a liquid within the barrel; and a processor configured to: receive the reflected signals; and determine a change in at least one characteristic of the return signal, wherein based on the determined change in the at least one characteristic an alcohol content may be determined. The processor may be further configured to: determine a loss of liquid within the barrel based on the determined level of fluid and an initial level of fluid; and limit the signal transmission from those antenna that would provide useful information in the estimation of an alcohol content of the liquid within the barrel.

The system may further comprise the processor may be configured to store the estimated alcohol content.

The system may further comprise the processor may be configured to extrapolate an expected alcohol content based on a stored plurality of estimated alcohol measures.

The system may further comprise the processor may be configured to adjust the estimated alcohol content based on at least one environmental condition.

The at least one environmental condition may be selected from a group consisting of: temperature, location within a facility, a geographic location of the facility, and container condition.

The determination of estimating the alcohol content may be performed periodically.

The rate of periodicity estimating the alcohol content may be adjustable.

The rate of periodicity estimating the alcohol content may be adjustable as a function of time.

An exemplary method may comprise: determining, by a monitoring system external to a container, an estimation of an alcohol content of the liquid within the container based on the a determination of one or more characteristic associated with one or more signals transmitted within the barrel, wherein the estimation comprises: determining a change in at least one characteristic at a known frequency (or phase); obtaining a first order alcohol content based on a model expectation of alcohol content at the known frequency (or phase); and determining the alcohol content based on adjusting the first order alcohol content based accumulating a plurality of first order alcohol content associated with different locations of fluid within the barrel or container.

The method may further comprise projecting an estimated alcohol content based on a plurality of the determined alcohol content.

The method may further comprise determining the alcohol content of the liquid within the container periodically, wherein measurements of the alcohol content are performed at a first rate during a first period of time and at a second rate during a second period of time, the first rate being faster than the second rate. The first rate and the second rate of the transmission of signals for the determination of alcohol content may be based, at least in part, as previously discussed with regard to the transmission of signals for the determination of fluid level. For example, the first rate may occur during a first period of time and the second rate may occur during a second period of time. The first rate may be greater than the second rate. For example, during a period of expected rapid change in alcohol content measurement associated with the determination of alcohol content, measurements may occur once/week, whereas during a period of expected slowing of the change in alcohol content, the determination of alcohol content may occur once/month, semi-annually, etc.

It would be understood and recognized that the first and second rates associated with fluid level measurement and alcohol content may be same or different. In addition, it would be recognized that the measurement of fluid level and alcohol content may be performed periodically wherein the period of measurement of fluid level and the period of determination of alcohol content may be the same or different. That is, fluid level measurement and alcohol content measurement may be performed at the same time and the same rates. Alternatively, fluid level measurement and alcohol content measurement may be performed at different times and at different rates.

In summary, the presented invention, provides for the determination of alcohol production progression during the distilling of an alcohol based liquid within a container without causing any interference with the alcohol production by the need to physically test the liquid, wherein the measure of alcohol with the container is based on a system that may be attached to a face of a container, that causes the transmission of one or more signals in at least one frequency range into the container, where the transmitted signals that are reflected off the fluid or liquid contained within the container are captured and evaluated to determine a level of the fluid or liquid within the tank. A measure of the alcohol content is then based on the determination of the loss of fluid or liquid.

The system disclosed achieves technical advantages over the prior art as the invention disclosed remains external to the enclosed system (barrel, etc.) and does not affect the internal ecosystem or contents of the barrel.

In addition, a method associated with the present invention is disclosed, wherein the method comprises the steps of: transmitting at least one signal into said tank; receiving a response associated with selected ones of said transmitted at least one signal; and evaluating said received response associated with selected ones of said transmitted at least one signal, wherein said evaluation comprises: determining a signal strength of each of said received response; selecting at least two of said received responses, wherein said selected responses are associated with a highest signal strength; and determining said fluid level based on a relationship between said selected at least two of said received responses.

In addition, a method associated with the present invention is disclosed wherein the method comprises the steps of: obtaining an initial alcohol content and level of a fluid within a container and obtaining measurements of the fluid level over time to evaluate and determine a loss of fluid due to one of evaporation and absorption, computing an expected alcohol content based on the initial alcohol content and the loss of fluid and further adjusting the expected alcohol content by one or more environment factors associated with at least the conditions surrounding the storage of the fluid.

Although various features have been described with reference to the Figures, other features are possible. For example, a device implementation in accordance with the present disclosure may comprise modular units with a varying thickness print flex antenna across a barrel face. The device may be implemented with a custom-designed PCB motherboard configured to be mounted in the middle of the barrel face. The device may comprise radar and radio frequency chips and a separate data transceiver module. The data transceiver module may be configured to operate using BLUETOOTH, LORAWAN or another band protocol. The device may be configured with a defined power source, for example a C1, D2 certified single core battery. The device may be attached to the face of an enclosed system (e.g., a whiskey barrel) with the printed antenna arrays located with reference to a defined position of a watch/barrel face. The antenna arrays may be located with reference to the center point of the watch/barrel face. The devices may be adhered or attached to the barrel face with an adhesive or attached with composite fasteners (screw/nail/staples, or the like).

The device may be configured to use a combination of Millimeter Wave (MM Wave) and or Radio Wave (RF), and/or other direct analog measurement methodologies to determine the liquid substrate level behind a barrel face. Liquid-level measurements may be relayed to multiple central communications hubs via BLUETOOTH, LORAWAN or any other communications technology, depending on the distance from the barrel to central device. From the central device, measurement data may be exported out of the rickhouse via satellite, cellular, or fiber connection to the cloud or a handheld device. A device implementation deployed on a barrel may be configured to broadcast measurement data packets from the barrel to the central device and from there exported out of the rickhouse via satellite, cellular, or fiber connection to the cloud or a handheld device configured to collect the measurement data packets exported from the central receiving device.

The device implementation may be configured to account for the introduction of foreign bodies or materials such as wooden staves, woods chips, or anything else that would displace the liquid level. For example, software may be configured to account for the displacement measurement and the displacement differential of any object inserted into the liquid to maintain an accurate measurement. In an illustrative example, the displacement and/or differential measurement software implementation may have a foreign body displacement measurement mode that determines displacement differential between liquid levels measured at different points in time, that is, before and after a foreign body is introduced to the container. The device implementation may incorporate the use of RFID to connect the device to software to track the device/barrel location in a "rickhouse."

The device implementation may use MM Wave, RF Wave, or another lower frequency or band as needed. This radar may be a low enough frequency to ensure penetration of the wood or the material associated with the container. The signal that is transmitted into the barrel by the antenna would be reflected back at levels where the liquid is present, in contrast with no reflections from levels where the liquid is not present. This group of reflections and non-reflections produces a total measured signal that is processed by the device to determine an estimate of the height of the liquid-air interface.

In an illustrative example a device implementation may be configured to determine liquid level measurements in a horizontal rick storage mode. For example, a horizontal rick storage mode implementation may be configured to measure the liquid level over time as it relates to where any substrate is in contact with the barrel face as well as the liquid-air interface. Such an implementation will be able to determine fluid volume at any given period. Distillers are required by law to log exactly how many proof gallons they put into any barrel at any time. The device implementation may be calibrated by inputting the exact amount of whiskey/tequila/spirits/etc. (substrate) reported to all required international governmental agencies on to the device, permitting the device to measure the differential of evaporation over time (AKA "The Angels Share"). In an illustrative example, the device implementation can then determine loss over time based on how antennas read the liquid-air interface behind each antenna. In this example implementation, the device is directly measuring the difference in liquid level between points of a varying printed antenna design as well as any liquid-air gaps in the antenna array which may vary in size and orientation.

In another illustrative example a device implementation may be configured to determine liquid level measurements in a vertical palletized storage mode. For example, a vertical palletized storage mode implementation may be configured to measure the reflection between the waves as it pertains to liquid content of an aging barrel. In this mode one or more antennas will reflect waves downward through the barrel face and measure the reflection time between device and barrel, device and substrate, device and barrel bottom as well as any materials inserted or placed in the barrel. This measurement may calculate the distance and relative length of the wave and convert that measure into an accurate measure of substrate. Some waves will go through the barrel and never return and will be disregarded. The device may be configured to only interpret what the device knows as operative space and measure total volume.

The device implementation may be a combination of a peel and stick design and/or with a potential non-metal/composite screw/staple/nail or fastening device that would allow distillers to adhere/attach the device to the barrel face at the time of barrel fill.

During barrel fill distillers are required by the law to exactly track and log the amount of liquid put in the barrel as stated above. All barrels may not be filled to the same fill level or amount. Accordingly, one or more calibration steps may be performed, as described herein. Connecting the device to the barrel and the system may benefit from calibration to ensure correct and accurate measurements. In an illustrative example a software application may be configured to uniquely associate the barrel to the device for the barrel's primary lifespan (these could be sent to a secondary market). For example, a unique hardware identifier for a barrel may be associated in a database with a unique identifier for an instance of the measurement device disclosed herein. In such an example, particular calibration data determined for the barrel/measurement device pair may be uniquely associated with the measurement device in the database, permitting the calibration and measurement performance of the device to be tracked over time.

As these "rickhouse" environments are quite harsh, a very strong adhesive or other fastening device may be used to adhere/attach the device to the barrel face in both horizontal (traditional rick storage) and vertical (palletized) storage options. We may also encase the designed PCB board and all of the components in a strong epoxy resin potting material or other hard casing to protect all electronics from any potential damage. Damage could be from forces like bumps, scrapes, dings to whiskey leaking on top and heat and/or humidity.

Once the barrel is filled and calibrated, the device is capable of providing a near absolute liquid level measurement. Barrels may range in total volume (the industry average is a 53-gallon barrel which will vary in finished size.) Barrels can be filled above 53 gallons. In an illustrative example the device may adhere/attach to the barrel face in the same fashion regardless of barrel size or storage options such as horizontal rick storage and palletized storage. Antenna arrays can vary in size and orientation based on the size of the barrel face as the barrels vary in total surface volume.

After filling, barrels may be moved to their storage locations where they will sit for varying periods of time. Because of this the device design may comprise a single core ATEX certified battery system which will give a potential life span between 6-10 years. In an illustrative example the device may be configured to satisfy a fire safety class 1 div 2 classifications according to DISCUS, NEC, and as well as ATEX class 2. Keeping fire safety in mind, the single core battery may be used because the single core battery traditionally has a slower discharge rate than reusable or rechargeable batteries. The device may be configured to ping only once a month, every month for the life span of the device or barrel, to conserve battery energy.

The device may be configured to be in communication with a central receiver. The central receiver may be configured in communication with other sensors such as ambient temperature and humidity. Once the device is pinged from the central receiver, the device will activate; once activated the device programming will cause the device to follow distinct operation sequences for horizontal storage and palletized storage device implementations.

In an illustrative example a device implementation designed for a horizontal storage mode in a traditional rickhouse may be configured to perform operations comprising: the device will activate an RF signal which goes across the antenna array; the device will measure exactly the differential of what is behind the barrel head and any relation to the space liquid-air differential between antennas across the clock face of the barrel and the device; as well as the relation of what's behind the wood to our antenna array will allow for volume measurement.

In an illustrative example a device implementation designed for a palletized storage mode may be configured to perform operations comprising: the device will activate in a similar manner as the horizontal storage mode implementation but rather with an MM signal. The device will fire downward and register the wavelength and reflection between device, barrel face, liquid, barrel bottom, and any particulate inside the barrel; the device will then interpret the total space of liquid contained and a measurement will be calculated.

All measurements will be saved in platform for the distiller or end user to make both qualitative and quantitative inferences. These qualitative and quantitative inferences may be used to calculate predictions for Barrel Yield, Tax Planning, Barrel Provenance, and Supply Chain planning.

If a distiller can understand exactly where their total run volume stands more accurately than current industry models of 2-4% loss per year they can make better decisions and inferences on metrics such as barrel performance as it relates to the quality of a cooperage (barrel maker), how any potential variable may affect a barrel such as heat, humidity, any coating material or R&D experiment. Knowing the volume of barrel can allow distillers to make many decisions to both increase efficiency and reduce industrial waste.

Another value add is that with the accurate volume, distillers can work with their insurance provider to reduce potential premiums as well as make sure that they are neither under-insured nor over-insured. They would just be adequately insured for loss.

Potential Yield: In the pursuit of optimizing production, distilleries need to and want to accurately gauge the volume of whiskey in each barrel. This not only helps in maximizing the yield from each batch but also in efficiently utilizing resources. Precise measurements allow for better supply chain forecasting and planning, ensuring that each step of the distillation and aging process is conducted with the utmost efficiency. Also helping with yield as it pertains to number of bottles and cases for their distributors.

Tax Planning: The taxation on distilled spirits can be complex, and it's based, in part, on the volume of product produced and stored. Accurate barrel measurements are essential for distilleries to comply with tax regulations accurately. This precision helps avoid over or underpayment of taxes, which can have significant financial implications. By knowing exactly how much whiskey is in each barrel, distilleries can file more accurate tax returns, thus avoiding potential legal and financial issues. There are major benefits to knowing your PGs (proof gallons) as tax rates do change from around $2.85 and $13.25 once a distillery crossed a set limit (100,000 PGs or roughly 1886 barrel) taxes increase.

Provenance: from its distillation to its aging—knowing volume and history adds to the product's allure and value consumers will pay. Precise barrel measurement contributes to the detailed tracking of each batch's journey, ensuring that the provenance is well-documented and authentic. This level of detail enriches the narrative of the whiskey, providing whiskey enthusiasts with a deeper appreciation of its heritage and quality.

The device may be implemented with a flex tail antenna array that will cover the clockface or in a wagon wheel design of a whiskey barrel that is adhered by a durable adhesive or composite fastener. RF and MM wave chips may be used to determine the liquid levels. The device may include a fire safety approved battery. The device may be configured with multiple interfaces to push data both into and out of the device. The device may be encased in a hard epoxy potting or protective casing. The device may be configured with BLUETOOTH, LORAWAN or another communication band to carry data in and out of the device.

The device remains external to the barrel and does not impede the aging process. The device lowers labor cost over handheld devices and is more accurate. The device is also on the face of the barrel; thus, the barrel can be rolled without the device having to be removed.

The device disclosed, while discussed with regard to a barrel or container associated with alcohol production, it would be recognized that the system and processing disclosed, herein, is applicable to other configurations, such as septic tank, waste management systems, water towers, or other similar type containers that are used to retain one or more content that may be a liquid, a mash and/or a solid (and combination thereof) to determine a level of the contained content, whether liquid, mash or solid within the configuration.

While examples of the operation of the invention have been presented, it would be understood that the examples using specific values are solely made for the purpose of providing information to those skilled in the art regarding the operation of the invention claimed and do not represent limiting values as to the scope of the subject matter of the invention as is recited in the claims.

For example, the invention disclosed may determine a level of a solid content within a septic tank, wherein the system comprises at least one transmitting antenna positioned on a face (or the lid) of the septic tank, the transmitting antenna configured to transmit into the tank a frequency modulated signal, wherein a starting frequency and a modulation of the signal is selected based on the material within the tank; and at least one receiving antenna configured to receive return signals corresponding to the transmitted frequency modulated signal, wherein the return signals are received within a time window associated with a corresponding transmitted signal, determining from a time of the received return signal with respect to the corresponding transmitted signal, a distance from the at least one transmitting antenna to the fill level of the solid content; and provide an indication of the fill level to at least one monitoring system, the monitoring system being one of: local to the system and remote from the system.

In still another example, the invention disclosed may monitor content within a container by transmitting signal downwardly into a container from a source positioned external to the container, a least one signal into the container, wherein the frequency of the at least one signal varies over time, determining a time of reception of a response with respect to the transmission, wherein the response is received within an expected time window after a time of transmission of a corresponding transmitted signal, determining a distance to at least one content within the container generating the based on the time of the return; and provide an indication of a level of fill of at least one of the at least one content within the container.

In one aspect of the invention, the frequency of transmission of each of the at least one signal is based, in part, of the content within the container, wherein a starting frequency of each of the at least one transmitted signal is based, in part, on the expected content with the container.

In one aspect of the invention, the variation of the frequency of the at least one transmitted signal is based, in part, on the expected content of the container, wherein the variation of frequency transmission is one of: continuous and patterned.

In one aspect of the invention, the transmission of the signal into the container may be arranged substantially perpendicular to a face of the container or transmitted at an angle to the expected content. In one aspect of the invention, an alarm may be triggered when a steepness of the angle of transmission falls below a known threshold.

In one aspect of the invention, providing an indication of a level of fill comprises transmitting the fill level to one of: a locally monitored memory storage device and to a remote location, wherein the transmission is through one of: a wired connection and a wireless connection.

In still another example, the invention disclosed may determine a level of at least one content within a container, wherein the system comprises at least one transmitting antenna and at least one receiving antenna positioned both of which may be positioned jointly or separately on a face of the barrel, wherein each of the at least one transmitting antenna is configured to transmit a signal in at least one frequency range with at least frequency variation during the transmission, each of the at least one receiving antenna configured to receive a corresponding response to the transmitted signal and a processing system comprising a processor and a memory containing therein processor readable instruction, which when accessed by the processor cause the processor to instruct each of the transmitting antenna to transmit the at least one signal, receive from a selected one of the plurality of receiving antenna a response from the transmitted at least one signal, wherein the response is received within an expected time window; determine a level of at least one content with the container; and provide an indication of the determined level for each of the at least one content within the container.

The invention has been described with reference to specific embodiments. One of ordinary skill in the art, however, appreciates that various modifications and changes can be made without departing from the scope of the invention as set forth in the claims. Accordingly, the specification is to be regarded in an illustrative manner, rather than with a restrictive view, and all such modifications are intended to be included within the scope of the invention.

Benefits, other advantages, and solutions to problems have been described above regarding specific embodiments. The benefits, advantages, and solutions to problems, and any element(s) that may cause any benefits, advantages, or solutions to occur or become more pronounced, are not to be construed as a critical, required, or an essential feature or element of any or all of the claims.

What is claimed is:

1. A method for monitoring content within a container, the method comprising:
    transmitting, from a source positioned external to the container, at least one signal into the container through an external surface thereof, wherein a frequency of the at least one signal varies over time;
    determining a time of reception of a response to the at least one transmitted signal, wherein the response is received within a time window defined to exclude signals arriving outside a predetermined range following transmission of the at least one signal;
    determining, based on the time of reception of the response received within the time window and the frequency variation of the at least one transmitted signal, a distance to at least one content within the container generating the response; and
    providing an indication of a level of fill of at least one of the at least one content within the container.

2. The method of claim 1, wherein the frequency variation of the at least one transmitted signal is based, in part, on the content within the container.

3. The method of claim 1, wherein a starting frequency of the at least one transmitted signal is based, in part, on expected content within the container.

4. The method of claim 3, wherein the frequency variation of the at least one transmitted signal is based, in part, on expected content of the container.

5. The method of claim 1, wherein the frequency variation is one of: continuous and patterned.

6. The method of claim 1, wherein the at least one transmitted signal is transmitted at an angle to the content.

7. The method of claim 6, wherein an alarm is triggered when a steepness of the angle of transmission falls below a threshold.

8. The method of claim 1, wherein providing the indication of the level of fill comprises:
    transmitting the fill level to at least one of: a locally monitored memory storage device, or a remote location, wherein the transmission is through at least one of: a wired connection or a wireless connection.

9. A system for determining a level of at least one content within a container, the system comprising:
    at least one transmitting antenna and at least one receiving antenna positioned on a face of the container, wherein each transmitting antenna is configured to transmit at least one signal into the container through an external surface thereof, wherein a frequency of the at least one signal varies over time during transmission, and each receiving antenna is configured to receive a corresponding response to the transmitted at least one signal; and
    a processing system comprising: at least one processor; and a memory containing processor readable instructions, which when accessed by the at least one processor cause the at least one processor to:
    instruct each transmitting antenna to transmit the at least one signal;
    receive, from a selected receiving antenna, a response to the transmitted at least one signal, wherein the response is received within a time window defined to exclude signals arriving outside a predetermined range following transmission of the at least one signal;
    determine a level of at least one content within the container based on a time of reception of the received response and the frequency variation of the transmitted at least one signal; and
    provide an indication of the determined level for each of the at least one content within the container.

10. The system of claim 9, wherein the at least one processor is further configured to cause transmission of the at least one signal from the at least one transmitting antenna periodically.

11. The system of claim 9, wherein a starting frequency of the transmitted at least one signal is based, in part, on an expected content within the container.

12. The system of claim 9, wherein the processing system is further configured to vary the frequency of transmission of the at last one transmitted signal.

13. The system of claim 9, wherein the processing system is configured to alter an angle of transmission of the at least one transmitted signal.

14. The system of claim 9, wherein the processing system is further configured to provide an alarm when the determined fill level exceeds a threshold.

15. The system of claim 9, wherein the at least one transmitting antenna and the at least one receiving antenna are physically separated along a face of the container.

16. The system of claim 9, wherein the time window defined for receiving a response decreases as the fill level of the at least one content increases.

17. The system of claim 16, wherein an angle of transmission decreases as the fill level of at least one content increases.

18. A system for determining a level of a at least one content within a container, the system comprising:
- at least one transmitting antenna positioned on a face of the container, the at least one transmitting antenna configured to transmit at least one signal downwardly into the container through an external surface thereof, wherein a frequency of the at least one signal varies over time during transmission; and
- at least one receiving antenna configured to receive a response corresponding to the at least one transmitted signal, wherein the response is received within a time window defined to exclude signals arriving outside a predetermined range following transmission of the corresponding signal; and
- a processing system comprising: at least one processor; and a memory containing processor readable instructions, which when accessed by the at least one processor, cause the at least one processor to:
  - determine, based on a time of reception of the response received within the time window and the frequency variation of the at least one transmitted signal, a distance from the at least one transmitting antenna positioned on the face of the container to the level of the at least one content within the container; and
  - provide an indication of the determined level of the at least one content to at least one monitoring system, the monitoring system being one of: local to the system or remote from the system.

19. The system of claim 18, wherein the container comprises one of: a barrel, a septic tank, a waste management container, or a water tower.

20. The system of claim 19, wherein at least one frequency range and a frequency variation of the at least one transmitted signal is based, in part, on an expected content within the container.

21. A system for determining a level of a solid content within a septic tank, the system comprising:
- at least one transmitting antenna positioned on a lid of the septic tank, the transmitting antenna configured to transmit at least one signal into the septic tank through an external surface thereof, wherein a frequency of the at least one signal varies over time during transmission, and wherein a starting frequency and a modulation profile of the at least one signal are selected based on the solid content within the septic tank; and
- at least one receiving antenna configured to receive a response corresponding to the at least one transmitted signal, wherein the response is received within a time window defined to exclude signals arriving outside a predetermined range following transmission of the corresponding signal; and
- a processing system comprising: at least one processor; and a memory containing processor readable instructions, which when accessed by the at least one processor cause, the at least one processor to:
  - determine, based on a time of reception of the response received within the time window and the frequency variation of the at least one transmitted signal, a distance from the at least one transmitting antenna to a level of the solid content within the septic tank; and
  - provide an indication of the determined level of the solid content within the septic tank to at least one monitoring system, the monitoring system being one of: local to the system or remote from the system.

* * * * *